United States Patent
Walsh

(10) Patent No.: US 10,653,619 B2
(45) Date of Patent: May 19, 2020

(54) DRUG DEPOTS FOR TREATMENT OF PAIN AND INFLAMMATION

(71) Applicant: Medtronic, Inc., Minneapolis, MN (US)

(72) Inventor: Andrew J. Lowenthal Walsh, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/223,571

(22) Filed: Dec. 18, 2018

(65) Prior Publication Data

US 2019/0110982 A1  Apr. 18, 2019

Related U.S. Application Data

(60) Continuation of application No. 15/280,381, filed on Sep. 29, 2016, now abandoned, which is a division of application No. 12/409,058, filed on Mar. 23, 2009, now abandoned.

(51) Int. Cl.

| | | |
|---|---|---|
| *A61K 9/00* | (2006.01) | |
| *A61K 9/70* | (2006.01) | |
| *A61K 31/192* | (2006.01) | |
| *A61K 31/4164* | (2006.01) | |
| *A61K 31/439* | (2006.01) | |
| *A61K 31/44* | (2006.01) | |
| *A61K 31/445* | (2006.01) | |
| *A61K 31/4523* | (2006.01) | |
| *A61K 31/56* | (2006.01) | |
| *A61F 13/20* | (2006.01) | |
| *A61F 13/84* | (2006.01) | |
| *A61K 31/135* | (2006.01) | |
| *A61K 31/4168* | (2006.01) | |
| *A61K 31/4468* | (2006.01) | |
| *A61K 31/451* | (2006.01) | |
| *A61K 31/4535* | (2006.01) | |
| *A61K 31/454* | (2006.01) | |
| *A61K 31/485* | (2006.01) | |
| *A61K 31/573* | (2006.01) | |
| *A61K 31/58* | (2006.01) | |
| *A61K 31/655* | (2006.01) | |
| *A61K 47/30* | (2006.01) | |
| *A61K 47/36* | (2006.01) | |
| *A61K 51/12* | (2006.01) | |

(52) U.S. Cl.
CPC ........ *A61K 9/0024* (2013.01); *A61F 13/2005* (2013.01); *A61F 13/8405* (2013.01); *A61K 9/0043* (2013.01); *A61K 9/7007* (2013.01); *A61K 31/135* (2013.01); *A61K 31/192* (2013.01); *A61K 31/4164* (2013.01); *A61K 31/4168* (2013.01); *A61K 31/439* (2013.01); *A61K 31/44* (2013.01); *A61K 31/445* (2013.01); *A61K 31/4468* (2013.01); *A61K 31/451* (2013.01); *A61K 31/454* (2013.01); *A61K 31/4523* (2013.01); *A61K 31/4535* (2013.01); *A61K 31/485* (2013.01); *A61K 31/56* (2013.01); *A61K 31/573* (2013.01); *A61K 31/58* (2013.01); *A61K 31/655* (2013.01); *A61K 47/30* (2013.01); *A61K 47/36* (2013.01); *A61K 51/1282* (2013.01)

(58) Field of Classification Search
CPC .......... A61K 9/14; A61K 9/141; A61K 9/143; A61K 9/145; A61K 9/146; A61K 9/16; A61K 9/1605; A61K 9/1652; A61K 9/167; A61K 9/1676; A61K 9/1682
See application file for complete search history.

(56) References Cited

U.S. PATENT DOCUMENTS

| | | |
|---|---|---|
| 3,020,660 A | 8/1964 | Zeile et al. |
| 3,190,802 A | 6/1965 | Zeile et al. |
| 4,624,255 A | 11/1986 | Schenck et al. |
| 4,692,147 A | 9/1987 | Duggan |
| 4,742,054 A | 5/1988 | Naftchi |
| 4,765,974 A | 8/1988 | Tokuda et al. |
| 4,863,457 A | 9/1989 | Lee |
| 5,175,052 A | 12/1992 | Tokuda et al. |
| 5,368,854 A | 11/1994 | Rennick |
| 5,368,859 A | 11/1994 | Dunn et al. |
| 5,447,947 A | 9/1995 | Campbell |
| 5,484,607 A | 1/1996 | Horacek |
| 5,512,055 A | 4/1996 | Domb et al. |
| 5,522,844 A | 6/1996 | Johnson |
| 5,626,838 A | 5/1997 | Cavanaugh et al. |
| 5,633,002 A | 5/1997 | Stricker et al. |
| 5,635,204 A | 6/1997 | Gervirtz et al. |
| 5,711,316 A | 1/1998 | Elsberry et al. |
| 5,759,583 A | 6/1998 | Iwamoto et al. |
| 5,762,638 A | 6/1998 | Skiani et al. |
| 5,801,188 A | 9/1998 | Hassenbusch, III et al. |

(Continued)

FOREIGN PATENT DOCUMENTS

| | | |
|---|---|---|
| EP | 1 405 646 | 4/2004 |
| EP | 1 462 111 | 9/2004 |

(Continued)

OTHER PUBLICATIONS

U.S. Appl. No. 12/424,271 (U.S. Pat. No. 8,889,173), filed Apr. 15, 2009 (Nov. 18, 2014), Alpha Adrenergic Receptor Agonists for Treatment of Pain and/or Inflammation.

(Continued)

*Primary Examiner* — Micah Paul Young
(74) *Attorney, Agent, or Firm* — Knobbe Martens Olson & Bear, LLP

(57) ABSTRACT

Effective treatments of pain and/or inflammation are provided. Through the administration of a porous biodegradable drug depot film, patch, strip or sponge being implantable within a nasal or sinus cavity and having pores sized to prevent the depot from functioning as a scaffold for tissue growth, one can reduce, prevent or treat pain and/or inflammation and prevent cells from infiltrating the drug depot and laying down scaffolding cells.

28 Claims, 4 Drawing Sheets

(56) References Cited

U.S. PATENT DOCUMENTS

| | | |
|---|---|---|
| 5,868,789 A | 2/1999 | Huebner |
| 5,869,100 A | 2/1999 | Horacek |
| 5,900,245 A | 5/1999 | Sawhney et al. |
| 5,942,241 A | 8/1999 | Chasin et al. |
| 5,942,503 A | 8/1999 | Jung et al. |
| 5,942,530 A | 8/1999 | Panetta et al. |
| 5,945,416 A | 8/1999 | Shannon et al. |
| 5,978,702 A | 11/1999 | Ward et al. |
| 5,980,927 A | 11/1999 | Nelson et al. |
| 6,030,642 A | 2/2000 | Horacek |
| 6,069,129 A | 5/2000 | Sandberg et al. |
| 6,083,919 A | 7/2000 | Johnson et al. |
| 6,093,180 A | 7/2000 | Elsberry |
| 6,147,102 A | 11/2000 | Borgman |
| 6,177,077 B1 | 1/2001 | Tobinick |
| 6,179,862 B1 | 1/2001 | Sawhney |
| 6,180,855 B1 | 1/2001 | Alexander et al. |
| 6,248,345 B1 | 6/2001 | Goldenheim |
| 6,272,370 B1 | 8/2001 | Gillies et al. |
| 6,277,413 B1 | 8/2001 | Sankaram |
| 6,287,588 B1 | 9/2001 | Shih et al. |
| 6,287,688 B1 | 9/2001 | Howell et al. |
| 6,306,424 B1 | 10/2001 | Vyakarnam et al. |
| 6,326,020 B1 | 12/2001 | Kohane et al. |
| 6,331,311 B1 | 12/2001 | Brodbeck et al. |
| 6,417,184 B1 | 7/2002 | Ockert |
| 6,428,804 B1 | 8/2002 | Suzuki et al. |
| 6,451,335 B1 | 9/2002 | Goldenheim et al. |
| 6,461,631 B1 | 10/2002 | Dunn et al. |
| 6,521,259 B1 | 2/2003 | Chasin et al. |
| 6,524,607 B1 | 2/2003 | Goldenheim et al. |
| 6,534,048 B1 | 3/2003 | Borgman |
| 6,534,081 B2 | 3/2003 | Goldenheim et al. |
| 6,589,549 B2 | 7/2003 | Shih et al. |
| 6,594,880 B2 | 7/2003 | Elsberry |
| 6,596,747 B2 | 7/2003 | Bos |
| 6,630,155 B1 | 10/2003 | Chandrashekar et al. |
| 6,632,457 B1 | 10/2003 | Sawhney |
| 6,723,741 B2 | 4/2004 | Jeon et al. |
| 6,756,058 B2 | 6/2004 | Brubaker et al. |
| 6,773,714 B2 | 8/2004 | Dunn et al. |
| 6,902,910 B2 | 6/2005 | Ni et al. |
| 6,921,541 B2 | 7/2005 | Chasin et al. |
| 6,974,462 B2 | 12/2005 | Sater |
| 6,992,110 B2 | 1/2006 | Kranzler et al. |
| 7,144,412 B2 | 12/2006 | Wolf et al. |
| 7,166,570 B2 | 1/2007 | Hunter et al. |
| 7,220,281 B2 | 5/2007 | Lambrecht et al. |
| 7,229,441 B2 | 6/2007 | Trieu |
| 7,235,043 B2 | 6/2007 | Gellman et al. |
| 7,287,983 B2 | 10/2007 | Ilan |
| 7,288,084 B2 | 10/2007 | Li |
| 7,318,840 B2 | 1/2008 | McKay |
| 7,329,259 B2 | 2/2008 | Cragg |
| 7,345,065 B2 | 3/2008 | Gil et al. |
| 7,361,168 B2 | 4/2008 | Makower et al. |
| 7,367,978 B2 | 5/2008 | Drewry |
| 7,418,292 B2 | 8/2008 | Shafer |
| 7,507,398 B2 | 3/2009 | Rabinowitz et al. |
| 7,524,812 B2 | 4/2009 | Ellis et al. |
| 7,717,848 B2 | 5/2010 | Heruth et al. |
| 7,727,954 B2 | 6/2010 | McKay |
| 7,741,273 B2 | 6/2010 | McKay |
| 7,964,585 B2 | 6/2011 | Berti-Mattera et al. |
| 7,993,666 B2 | 8/2011 | McKay et al. |
| 8,029,478 B2 | 10/2011 | Zanella |
| 8,202,531 B2 | 6/2012 | McKay et al. |
| 8,231,891 B2 | 7/2012 | McKay |
| 8,357,388 B2 | 1/2013 | McKay |
| 8,420,114 B2 | 4/2013 | Zanella et al. |
| 8,470,360 B2 | 6/2013 | McKay |
| 8,475,823 B2 | 7/2013 | Hobot et al. |
| 8,481,064 B2 | 7/2013 | McKay |
| 8,524,267 B2 | 9/2013 | Zanella et al. |
| 8,557,271 B2 | 10/2013 | Kimble et al. |
| 8,557,273 B2 | 10/2013 | McDonald et al. |
| 8,591,935 B2 | 11/2013 | McKay et al. |
| 8,617,583 B2 | 12/2013 | King |
| 8,623,396 B2 | 1/2014 | Gray et al. |
| 8,629,172 B2 | 1/2014 | McKay et al. |
| 8,722,079 B2 | 5/2014 | King |
| 8,735,504 B2 | 5/2014 | Clay |
| 8,822,546 B2 | 9/2014 | Benz et al. |
| 8,846,068 B2 | 9/2014 | Wohabrebbi et al. |
| 8,877,226 B2 | 11/2014 | Zanella et al. |
| 8,883,768 B2 | 11/2014 | Zanella et al. |
| 8,889,173 B2 | 11/2014 | Zanella et al. |
| 8,940,315 B2 | 1/2015 | Hobot et al. |
| 8,946,277 B2 | 2/2015 | Zanella et al. |
| 8,956,636 B2 | 2/2015 | Wohabrebbi et al. |
| 8,956,641 B2 | 2/2015 | Zanella et al. |
| 8,956,642 B2 | 2/2015 | Hobot et al. |
| 8,968,767 B2 | 3/2015 | McKay |
| 8,969,397 B2 | 3/2015 | Burright et al. |
| 8,980,317 B2 | 3/2015 | King |
| 8,999,368 B2 | 4/2015 | McDonald et al. |
| 9,005,634 B2 | 4/2015 | McDonald et al. |
| 9,040,532 B2 | 5/2015 | Chow et al. |
| 9,050,274 B2 | 6/2015 | Haddock et al. |
| 9,066,853 B2 | 6/2015 | Clay |
| 9,072,727 B2 | 7/2015 | McKay |
| 9,125,917 B2 | 9/2015 | McKay et al. |
| 9,132,085 B2 | 9/2015 | McDonald et al. |
| 9,132,119 B2 | 9/2015 | Hobot et al. |
| 9,211,274 B2 | 12/2015 | Moore et al. |
| 9,211,285 B2 | 12/2015 | McKay et al. |
| 9,242,004 B2 | 1/2016 | Clay |
| 9,265,733 B2 | 2/2016 | McKay |
| 9,289,409 B2 | 3/2016 | Zanella et al. |
| 9,301,946 B2 | 4/2016 | Wilsey et al. |
| 9,351,959 B2 | 5/2016 | McKay |
| 9,358,223 B2 | 6/2016 | King |
| 9,375,420 B2 | 6/2016 | King |
| 9,387,197 B2 | 7/2016 | King |
| 9,492,461 B2 | 11/2016 | King et al. |
| 9,511,018 B2 | 12/2016 | Clay et al. |
| 9,549,920 B2 | 1/2017 | Wohabrebbi et al. |
| 9,556,333 B2 | 1/2017 | Clay |
| 9,585,872 B2 | 3/2017 | Zanella et al. |
| 9,610,243 B2 | 4/2017 | Clay et al. |
| 9,623,222 B2 | 4/2017 | McKay |
| 9,700,567 B2 | 7/2017 | Zanella et al. |
| 9,763,917 B2 | 9/2017 | Zanella et al. |
| 9,763,966 B2 | 9/2017 | McKay et al. |
| 9,770,438 B2 | 9/2017 | Hobot et al. |
| 9,775,800 B2 | 10/2017 | McDonald et al. |
| 9,833,548 B2 | 12/2017 | McKay et al. |
| 9,867,910 B2 | 1/2018 | Clay |
| 9,968,572 B2 | 5/2018 | Wilsey et al. |
| 2001/0004456 A1 | 6/2001 | Tobinick |
| 2001/0016195 A1 | 8/2001 | Tobinick |
| 2001/0018075 A1 | 8/2001 | Shigeyuki et al. |
| 2001/0026801 A1 | 10/2001 | Tobinick |
| 2002/0009454 A1 | 1/2002 | Boone et al. |
| 2002/0013298 A1 | 1/2002 | Hunter |
| 2002/0058656 A1 | 5/2002 | Ockert |
| 2002/0064547 A1 | 5/2002 | Chern et al. |
| 2002/0071822 A1 | 6/2002 | Uhrich |
| 2002/0077294 A1 | 6/2002 | Kay et al. |
| 2002/0090398 A1 | 7/2002 | Dunn et al. |
| 2002/0094998 A1 | 7/2002 | Burke et al. |
| 2002/0111603 A1 | 8/2002 | Cheikh |
| 2002/0131954 A1 | 9/2002 | Tobinick |
| 2002/0131955 A1 | 9/2002 | Tobinick |
| 2003/0007972 A1 | 1/2003 | Tobinick |
| 2003/0009145 A1 | 1/2003 | Struijker-Boudier et al. |
| 2003/0022926 A1 | 1/2003 | Lavand'Homme |
| 2003/0049256 A1 | 3/2003 | Tobinick |
| 2003/0077641 A1 | 4/2003 | Laskowitz et al. |
| 2003/0113318 A1 | 6/2003 | Tobinick |
| 2003/0118692 A1 | 6/2003 | Wang et al. |
| 2003/0119017 A1 | 6/2003 | McSwiggen |
| 2003/0144570 A1 | 7/2003 | Hunter et al. |
| 2003/0157061 A1 | 8/2003 | Bennett |

(56) References Cited

U.S. PATENT DOCUMENTS

| | | |
|---|---|---|
| 2003/0166559 A1 | 9/2003 | Desjarlais et al. |
| 2003/0175793 A1 | 9/2003 | Bennett et al. |
| 2003/0185826 A1 | 10/2003 | Tobinick |
| 2003/0185872 A1 | 10/2003 | Kochinke |
| 2003/0185873 A1 | 10/2003 | Chasin et al. |
| 2003/0204191 A1 | 10/2003 | Sater et al. |
| 2003/0216714 A1 | 11/2003 | Gill |
| 2003/0224033 A1 | 12/2003 | Li et al. |
| 2004/0028726 A1 | 2/2004 | Fischer et al. |
| 2004/0034357 A1 | 2/2004 | Beane et al. |
| 2004/0052384 A1 | 3/2004 | Ashley |
| 2004/0072799 A1 | 4/2004 | Li et al. |
| 2004/0082540 A1 | 4/2004 | Hermida Ochoa |
| 2004/0101582 A1 | 5/2004 | Wolicki |
| 2004/0109893 A1 | 6/2004 | Chen et al. |
| 2004/0208917 A1 | 10/2004 | Fischer et al. |
| 2004/0214793 A1 | 10/2004 | Hermida Ochoa |
| 2004/0119266 A1 | 11/2004 | Tuschl et al. |
| 2004/0259247 A1 | 12/2004 | Tuschl et al. |
| 2004/0259248 A1 | 12/2004 | Tuschl et al. |
| 2004/0265364 A1 | 12/2004 | Ozturk et al. |
| 2005/0026979 A1 | 2/2005 | Ghazzi et al. |
| 2005/0043706 A1 | 2/2005 | Eaton et al. |
| 2005/0058696 A1 | 3/2005 | Donello et al. |
| 2005/0059744 A1 | 3/2005 | Donello et al. |
| 2005/0075701 A1 | 4/2005 | Shafer |
| 2005/0079202 A1 | 4/2005 | Chen et al. |
| 2005/0090549 A1 | 4/2005 | Hildebrand et al. |
| 2005/0095246 A1 | 5/2005 | Shafer |
| 2005/0095277 A1 | 5/2005 | Ozturk et al. |
| 2005/0129731 A1 | 6/2005 | Horres et al. |
| 2005/0142163 A1 | 6/2005 | Hunter et al. |
| 2005/0175709 A1 | 8/2005 | Baty, III et al. |
| 2005/0177135 A1 | 8/2005 | Hildebrand et al. |
| 2005/0180974 A1 | 8/2005 | Shafer |
| 2005/0182009 A1 | 8/2005 | McSwiggen et al. |
| 2005/0186261 A1 | 8/2005 | Avelar et al. |
| 2005/0197293 A1 | 9/2005 | Mellis et al. |
| 2005/0197312 A1 | 9/2005 | Fitzgerald et al. |
| 2005/0209513 A1 | 9/2005 | Heruth et al. |
| 2005/0245557 A1 | 11/2005 | Schoenhard et al. |
| 2005/0245905 A1 | 11/2005 | Schmidt et al. |
| 2005/0288620 A1 | 12/2005 | Shippert |
| 2006/0013802 A1 | 1/2006 | Shafer |
| 2006/0046960 A1 | 3/2006 | McKay et al. |
| 2006/0046961 A1 | 3/2006 | McKay et al. |
| 2006/0074422 A1 | 4/2006 | Story et al. |
| 2006/0093602 A1 | 5/2006 | Life et al. |
| 2006/0106361 A1 | 5/2006 | Muni et al. |
| 2006/0148903 A1 | 7/2006 | Burch et al. |
| 2006/0153815 A1 | 7/2006 | Seyda et al. |
| 2006/0173060 A1 | 8/2006 | Chang et al. |
| 2006/0183786 A1 | 8/2006 | Wang |
| 2006/0189564 A1 | 8/2006 | Burright et al. |
| 2006/0189944 A1 | 8/2006 | Campbell et al. |
| 2006/0204548 A1 | 9/2006 | Nivaggioli et al. |
| 2006/0228391 A1 | 10/2006 | Seyedin et al. |
| 2006/0253100 A1 | 11/2006 | Burright et al. |
| 2006/0280797 A1 | 12/2006 | Shoichet et al. |
| 2007/0004790 A1 | 1/2007 | Chow |
| 2007/0005094 A1 | 1/2007 | Eaton et al. |
| 2007/0021358 A1 | 1/2007 | Edelman et al. |
| 2007/0031472 A1 | 2/2007 | Huang et al. |
| 2007/0031844 A1 | 2/2007 | Khvorova et al. |
| 2007/0066864 A1 | 3/2007 | Forde et al. |
| 2007/0104769 A1 | 5/2007 | Feng et al. |
| 2007/0156180 A1 | 7/2007 | Jaax et al. |
| 2007/0178138 A1 | 8/2007 | Pal et al. |
| 2007/0185497 A1 | 8/2007 | Cauthen et al. |
| 2007/0202074 A1 | 8/2007 | Shalaby |
| 2007/0225544 A1 | 9/2007 | Vance et al. |
| 2007/0243225 A1 | 10/2007 | McKay |
| 2007/0243228 A1 | 10/2007 | McKay |
| 2007/0248639 A1 | 10/2007 | Demopulos et al. |
| 2007/0253994 A1 | 11/2007 | Hildebrand |
| 2007/0292473 A1 | 12/2007 | Cheikh |
| 2008/0009830 A1 | 1/2008 | Fujimoto et al. |
| 2008/0014066 A1 | 1/2008 | Burright et al. |
| 2008/0020076 A1 | 1/2008 | Jhamandas |
| 2008/0021074 A1 | 1/2008 | Cartt |
| 2008/0038351 A1 | 2/2008 | Beals et al. |
| 2008/0075777 A1 | 3/2008 | Kennedy |
| 2008/0091207 A1 | 4/2008 | Truckai et al. |
| 2008/0095831 A1 | 4/2008 | McGraw |
| 2008/0152709 A1 | 6/2008 | Bortz |
| 2008/0171075 A1 | 7/2008 | Ozturk et al. |
| 2008/0317805 A1 | 12/2008 | McKay et al. |
| 2009/0017090 A1 | 1/2009 | Arensdorf et al. |
| 2009/0020076 A1 | 1/2009 | Ghiraldi |
| 2009/0156980 A1 | 6/2009 | Eaton et al. |
| 2009/0214612 A1 | 8/2009 | Shafer |
| 2009/0263443 A1 | 10/2009 | McKay et al. |
| 2009/0263448 A1* | 10/2009 | Hobot .................. A61K 9/0019 424/423 |
| 2009/0263451 A1 | 10/2009 | King et al. |
| 2009/0263459 A1 | 10/2009 | King et al. |
| 2009/0263489 A1 | 10/2009 | Zanella |
| 2009/0264477 A1 | 10/2009 | Zanella et al. |
| 2009/0264478 A1 | 10/2009 | Cox et al. |
| 2009/0264489 A1 | 10/2009 | Hildebrand et al. |
| 2010/0015049 A1 | 1/2010 | Wohabrebbi et al. |
| 2010/0021516 A1* | 1/2010 | McKay ................ A61K 9/0024 424/422 |
| 2010/0098746 A1 | 4/2010 | King |
| 2010/0159015 A1 | 6/2010 | Burright et al. |
| 2010/0203102 A1 | 8/2010 | Wohabrebbi et al. |
| 2010/0228097 A1 | 9/2010 | McKay |
| 2010/0239632 A1 | 9/2010 | Walsh |
| 2011/0027331 A1 | 2/2011 | Hobot |
| 2011/0097375 A1 | 4/2011 | King |
| 2011/0097380 A1 | 4/2011 | King et al. |
| 2011/0106110 A1 | 5/2011 | McKay |
| 2011/0313393 A1 | 12/2011 | Zanella |
| 2012/0029042 A1 | 2/2012 | King |
| 2012/0142648 A1 | 6/2012 | Biggs et al. |
| 2012/0142747 A1 | 6/2012 | Wilsey et al. |
| 2013/0217673 A1 | 8/2013 | Wilsey |
| 2014/0336162 A1 | 11/2014 | McKay et al. |
| 2015/0174104 A1 | 6/2015 | Burright |
| 2015/0342964 A1 | 12/2015 | Gray et al. |
| 2016/0095829 A1 | 4/2016 | Moore et al. |
| 2017/0014337 A1 | 1/2017 | Walsh |
| 2019/0076403 A1 | 3/2019 | Burright et al. |
| 2019/0083464 A1 | 3/2019 | Burright et al. |

FOREIGN PATENT DOCUMENTS

| | | |
|---|---|---|
| WO | WO 1993/001717 | 2/1993 |
| WO | WO 1993/005788 | 4/1993 |
| WO | WO 1997/042990 | 11/1997 |
| WO | WO 1997/044057 | 11/1997 |
| WO | WO 1998/020868 | 5/1998 |
| WO | WO 1998/047502 | 10/1998 |
| WO | WO 2001/008717 | 2/2001 |
| WO | WO 2002/009768 | 2/2002 |
| WO | WO 2002/100330 | 2/2002 |
| WO | WO 2002/038035 | 5/2002 |
| WO | WO 2002/070007 | 9/2002 |
| WO | WO 2002/074301 | 9/2002 |
| WO | WO 2002/080893 | 10/2002 |
| WO | WO 2002/085428 | 10/2002 |
| WO | WO 2003/005961 | 1/2003 |
| WO | WO 2003/026479 | 4/2003 |
| WO | WO 2003/070897 | 8/2003 |
| WO | WO 2003/070970 | 8/2003 |
| WO | WO 2003/072135 | 9/2003 |
| WO | WO 2003/083061 | 9/2003 |
| WO | WO 2003/099298 | 12/2003 |
| WO | WO 2004/005551 | 1/2004 |
| WO | WO 2004/032718 | 4/2004 |
| WO | WO 2004/039355 | 5/2004 |
| WO | WO 2004/066996 | 8/2004 |
| WO | WO 2004/091540 | 10/2004 |
| WO | WO 2004/100987 | 11/2004 |

(56) References Cited

FOREIGN PATENT DOCUMENTS

| WO | WO 2005/000278 | 1/2005 |
|---|---|---|
| WO | WO 2005/034998 | 4/2005 |
| WO | WO 2005/037323 | 4/2005 |
| WO | WO 2005/039393 | 5/2005 |
| WO | WO 2005/046708 | 5/2005 |
| WO | WO 2005/059134 | 6/2005 |
| WO | WO 2005/073164 | 8/2005 |
| WO | WO 2005/084366 | 9/2005 |
| WO | WO 2005/110362 | 11/2005 |
| WO | WO 2006/011915 | 2/2006 |
| WO | WO 2006/022611 | 3/2006 |
| WO | WO 2006/036280 | 4/2006 |
| WO | WO 2006/101540 | 9/2006 |
| WO | WO 2007/005177 | 1/2007 |
| WO | WO 2008/014066 | 1/2008 |
| WO | WO 2008/079868 | 7/2008 |
| WO | WO 2009/100441 | 8/2009 |
| WO | WO 2011/133370 | 10/2011 |
| WO | WO 2011/139595 | 11/2011 |

OTHER PUBLICATIONS

U.S. Appl. No. 12/412,024 (U.S. Pat. No. 9,132,119), filed Mar. 26, 2009 (Sep. 15, 2015), Clonidine Formulation in a Polyorthoester Carrier.
U.S. Appl. No. 14/852,039 (U.S. Pat. No. 9,770,438), filed Sep. 11, 2015 (Sep. 26, 2017), Clonidine Formulation in a Polyorthoester Carrier.
U.S. Appl. No. 12/426,031 (U.S. Pat. No. 8,940,315), filed Apr. 17, 2009 (Jan. 27, 2015), Benzodiazepine Formulation in a Polyorthoester Carrier.
U.S. Appl. No. 14/608,956 (U.S. Pat. No. 9,763,917), filed Jan. 29, 2015 (Sep. 19, 2017), Clonidine Formulations in a Biodegradable Polymer Carrier.
U.S. Appl. No. 14/608,981 (U.S. Pat. No. 9,585,872), filed Jan. 29, 2015 (Mar. 7, 2017), Clonidine Formulations in a Biodegradable Polymer Carrier.
U.S. Appl. No. 13/841,481 (U.S. Pat. No. 9,610,243), filed Mar. 15, 2013 (Apr. 4, 2017), Clonidine Compounds in a Biodegradable Polymer.
U.S. Appl. No. 16/374,300, filed Apr. 3, 2019, Clonidine Compounds in a Biodegradable Polymer.
U.S. Appl. No. 12/409,058, filed Mar. 23, 2009, Drug Depots for Treatment of Pain and Inflammation in Sinus and Nasal Cavities or Cardiac Tissue.
U.S. Appl. No. 15/280,381, filed Sep. 29, 2016, Drug Depots for Treatment of Pain and Inflammation in Sinus and Nasal Cavaties.
U.S. Appl. No. 12/410,151 (U.S. Pat. No. 8,557,273), filed Mar. 24, 2009 (Oct. 15, 2013), Medical Devices and Methods Including Polymers Having Biologically Active Agents Therein.
U.S. Appl. No. 13/934,375 (U.S. Pat. No. 8,999,368), filed Jul. 3, 2013 (Apr. 7, 2015), Medical Devices and Methods Including Polymers Having Biologically Active Agents Therein.
U.S. Appl. No. 12/421,108, filed Apr. 17, 2009, Methods and Compositions for Treating Postoperative Pain Comprising Clonidine.
U.S. Appl. No. 12/421,144 (U.S. Pat. No. 8,629,172), filed Apr. 9, 2009 (Jan. 14, 2014), Methods and Compositions for Treating Post-Operative Pain Comprising Clonidine.
U.S. Appl. No. 14/097,983 (U.S. Pat. No. 9,211,285), filed Dec. 5, 2013 (Dec. 15, 2015), Methods and Compositions for Treating Post-Operative Pain Comprising Clonidine.
U.S. Appl. No. 14/968,305 (U.S. Pat. No. 9,833,548), filed Dec. 14, 2015 (Dec. 5, 2017), Methods and Compositions for Treating Post-Operative Pain Comprising Clonidine.
U.S. Appl. No. 10/972,157, filed Oct. 22, 2004, Techniques to Treat Neurological Disorders by Attenuating the Production of Pro-Inflammatory Mediators.
U.S. Appl. No. 10/972,177, filed Oct. 22, 2004, Extracellular TNF Inhibitors for Treating CNS Disorders.
U.S. Appl. No. 12/463,065, filed May 8, 2009, Extracellular TNF Inhibitors for Treating CNS Disorders.
U.S. Appl. No. 11/460,012, filed Jul. 26, 2006, Systems and Methods to Treat Pain Locally.
U.S. Appl. No. 12/701,261 (U.S. Pat. No. 8,969,397), filed Feb. 5, 2010 (Mar. 3, 2015), Systems and Methods to Treat Pain Locally.
U.S. Appl. No. 14/635,637, filed Mar. 2, 2015, Systems and Methods to Treat Pain Locally.
U.S. Appl. No. 16/184,089, filed Nov. 8, 2018, Systems and Methods to Treat Pain Locally.
U.S. Appl. No. 16/184,092, filed Nov. 8, 2018, Systems and Methods to Treat Pain Locally.
U.S. Appl. No. 11/388,891, filed Mar. 24, 2006, Methods and Sequences to Suppress Pro-Inflamatory Cytokine Actions Locally to Treat Pain.
U.S. Appl. No. 12/424,368 (U.S. Pat. No. 8,420,114), filed Apr. 15, 2009 (Apr. 16, 2013), Alpha and Beta Adrenergic Receptor Agonists for Treatment of Pain and / or Inflammation.

\* cited by examiner

DRUG DEPOTS FOR TREATMENT OF PAIN AND INFLAMMATION

CROSS REFERENCE TO RELATED APPLICATIONS

This application is a continuation of U.S. patent application Ser. No. 15/280,381, filed Sep. 29, 2016, which is a divisional of U.S. patent application Ser. No. 12/409,058, filed Mar. 23, 2009, the entire disclosure of each of which is incorporated herein by reference.

BACKGROUND

Pain and inflammation relief is of prime importance to anyone treating patients undergoing surgery. Proper pain and inflammation relief imparts significant physiological and psychological benefits to the patient. Not only does effective pain and inflammation relief mean a smoother more pleasant postoperative course (e.g., mood, sleep, quality of life, etc.) with earlier discharge from medical/surgical/outpatient facilities, but it may also reduce the onset of chronic pain and inflammation syndromes (e.g., fibromyalgia, myalgia, etc.).

Pain serves a biological function. It often signals the presence of damage or disease within the body and is often accompanied by inflammation (redness, swelling, and/or burning). In the case of postoperative pain and inflammation it may be a result of the surgery, or other treatments such as, for example, management of acute pain following burns or non-surgical trauma. The goal for postoperative pain and inflammation management is to reduce or eliminate pain and inflammation discomfort with medication that cause minimum or no side effects.

The site of the surgery has a profound effect upon the degree of postoperative pain and inflammation a patient may suffer. In general, operations on the thorax and upper abdomen are more painful and have more inflammation than operations on the lower abdomen, which in turn are more painful and have more inflammation than peripheral operations on the limbs. However, any operation involving a body cavity, large joint surfaces, the spine or deep tissues should be regarded as painful and have some degree of inflammation. In particular, operations on the thorax or upper abdomen may produce widespread changes in pulmonary function, an increase in abdominal muscle tone and an associated decrease in diaphragmatic function. The result will be an inability to cough and clear secretions, which may lead to lung collapse and pneumonia. Prolonged pain and inflammation can reduce physical activity and lead to venous stasis and an increased risk of deep vein thrombosis and consequently pulmonary embolism. In addition, there can be widespread effects on gut and urinary tract motility, which may lead in turn to postoperative ileus, nausea, vomiting and urinary retention. These problems are unpleasant for the patient and may prolong hospital stay. Most patients who experience moderate to severe postoperative pain and inflammation often require pain and inflammation control at least in the first 3 days after trauma or surgery.

One area that is ripe for pain and/or inflammation due to trauma or surgery is the nasal and sinus cavities. Physicians are frequently called upon to treat nasal and sinus cavities as a result of tissue desiccation, trauma, infection, or other nasal and sinus diseases. Another area that is also affected by pain and inflammation is cardiac tissue. For example, during a myocardial infarction, commonly known as a heart attack, the blood supply to part of the heart is interrupted. The resulting ischemia (restriction in blood supply) and oxygen shortage, if left untreated for a sufficient period, can cause damage and/or death (infarction) of heart muscle tissue resulting in pain and inflammation.

Many treatment options for nasal, sinus and cardiac tissues involve administering analgesic and/or anti-inflammatory medications by oral and parenteral routes (e.g., intramuscular or intravenous, subcutaneous routes). These routes for drug administration often result in off target effects, which can cause increased adverse side effects.

Unfortunately, currently available analgesics and/or anti-inflammatory formulations, although effective for short term relief of pain and/or inflammation, require frequent single dose administration every 4 to 12 hours on an as needed basis. These single dose analgesics and/or anti-inflammatory formulations are inconvenient and may interfere with the patient's postoperative inpatient and/or outpatient daytime activities and nighttime sleep and recovery.

New analgesics and/or anti-inflammatory compositions and methods are needed to treat or reduce postoperative pain and/or inflammation at or near cardiac tissue or within the nasal or sinus cavity. New analgesics and/or anti-inflammatory compositions and methods that reliably provide long acting analgesic and anti-inflammatory effects over periods of 3 to 10 days are needed.

SUMMARY

New compositions and methods are provided that effectively prevent, treat or reduce postoperative pain or inflammation in areas at or near cardiac tissue or within the nasal or sinus cavity. In various embodiments, analgesic and/or anti-inflammatory compositions and methods are provided that have long acting analgesic and/or anti-inflammatory effects over periods of 3 to 10 days in a single drug depot or multiple drug depots. New drug depot films and methods are provided, which can easily allow accurate and precise implantation of a drug depot containing analgesic and/or anti-inflammatory compositions. One advantage of the analgesic and/or anti-inflammatory drug depot compositions and methods is that the drug depot can now be easily delivered to the target tissue site (e.g., nasal, sinus and/or cardiac tissue, surgical wound or incision, etc.) and provide pain relief for 3 to 10 days. In this way, accurate and precise implantation of the drug depot can be accomplished. In some embodiments, the drug depot is in the form of a film and can be locally delivered to the nasal, sinus and/or cardiac tissue by packing the drug depot at the target tissue site.

In one embodiment, an implantable drug depot is provided useful for reducing, preventing or treating pain and/or inflammation in a patient in need of such treatment, the implantable drug depot being in the form of a biodegradable film and comprising a therapeutically effective amount of an analgesic and/or an anti-inflammatory agent, the depot being implantable at or near a cardiac tissue or within the nasal or sinus cavity to reduce, prevent or treat pain and/or inflammation, wherein the drug depot is capable of releasing an effective amount of the analgesic and/or an anti-inflammatory agent over a period of at least one day.

In another embodiment, a method of treating or preventing pain and inflammation in a patient in need of such treatment is provided, the method comprising administering one or more biodegradable drug depots comprising a therapeutically effective amount of an analgesic and an anti-inflammatory agent at or near a cardiac tissue or within the nasal or sinus cavity to reduce, prevent or treat pain and/or inflammation, wherein the drug depot is in the form of a biodegradable film or strip that releases an effective amount of the analgesic and the anti-inflammatory agent or pharmaceutically acceptable salts thereof over a period of at least 1 day.

In yet another embodiment, a method is provided for reducing pain and inflammation in a patient in need of such treatment, the method comprising delivering one or more biodegradable drug depots in the form of a biodegradable film comprising a therapeutically effective amount of an analgesic and an anti-inflammatory agent or pharmaceutically acceptable salts thereof at or near a cardiac tissue or within the nasal or sinus cavity of the patient, wherein the drug depot releases an effective amount of the analgesic and the anti-inflammatory agent or pharmaceutically acceptable salts thereof over a period of at least 1 day.

The therapeutic agent may for example, be part of a drug depot. The drug depot may: (i) consist of the analgesic and/or an anti-inflammatory agent and the biodegradable polymer(s); or (ii) consist essentially of the analgesic and/or an anti-inflammatory agent; or (iii) comprise the analgesic and/or an anti-inflammatory agent and one or more other active ingredients, surfactants, excipients or other ingredients or combinations thereof. When there are other active ingredients, surfactants, excipients or other ingredients or combinations thereof in the formulation, in some embodiments these other compounds or combinations thereof comprise less than 20 wt. %, less than 19 wt. %, less than 18 wt. %, less than 17 wt. %, less than 16 wt. %, less than 15 wt. %, less than 14 wt. %, less than 13 wt. %, less than 12 wt. %, less than 11 wt. %, less than 10 wt. %, less than 9 wt. %, less than 8 wt. %, less than 7 wt. %, less than 6 wt. %, less than 5 wt. %, less than 4 wt. %, less than 3 wt. %, less than 2 wt. %, less than 1 wt. % or less than 0.5 wt. %.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

Figure 1A:
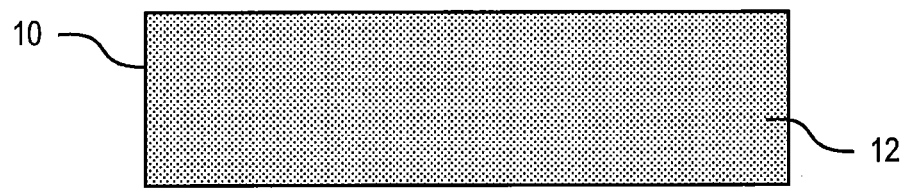
FIG. 1A illustrates a magnified top view of one embodiment of the implantable drug depot in the form of a film or strip that has the analgesic and/or an anti-inflammatory agent disposed on or in the film or strip.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

The headings below are not meant to limit the disclosure in any way; embodiments under any one heading may be used in conjunction with embodiments under any other heading.

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

New compositions and methods are provided that effectively prevent, treat or reduce postoperative pain or inflammation in areas at or near cardiac tissue or within the nasal or sinus cavity. In various embodiments, analgesic and/or anti-inflammatory compositions and methods are provided that have long acting analgesic and/or anti-inflammatory effects over periods of 3 to 10 days in a single drug depot or multiple drug depots. New drug depot films and methods are provided, which can easily allow accurate and precise implantation of a drug depot containing analgesic and/or anti-inflammatory compositions. One advantage of the analgesic and/or anti-inflammatory drug depot compositions and methods is that the drug depot can now be easily delivered to the target tissue site (e.g., nasal, sinus and/or cardiac tissue, surgical wound or incision, etc.) and provide pain relief for 3 to 10 days. In this way, accurate and precise implantation of the drug depot can be accomplished. In some embodiments, the drug depot is in the form of a film and can be locally delivered to the nasal, sinus and/or cardiac tissue by packing the drug depot at the target tissue site.

In one embodiment, an implantable drug depot is provided useful for reducing, preventing or treating pain and/or inflammation in a patient in need of such treatment, the implantable drug depot being in the form of a biodegradable film and comprising a therapeutically effective amount of an analgesic and/or an anti-inflammatory agent, the depot being implantable at or near a cardiac tissue or within the nasal or sinus cavity to reduce, prevent or treat pain and/or inflammation, wherein the drug depot is capable of releasing an effective amount of the analgesic and/or an anti-inflammatory agent over a period of at least one day.

Definitions

It is noted that, as used in this specification and the appended claims, the singular forms "a," "an," and "the," include plural referents unless expressly and unequivocally limited to one referent. Thus, for example, reference to "a drug depot" includes one, two, three or more drug depots.

Analgesic refers to an agent or compound that can reduce, relieve or eliminate pain. Examples of analgesic agents include but are not limited to acetaminophen, a local anesthetic, such as for example, lidocaine, bupivicaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The phrase "anti-inflammatory agent" refers to an agent or compound that has anti-inflammatory effects. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketorolac, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

An anti-inflammatory agent can be a steroid. Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

Examples of a useful statin for treatment of pain and/or inflammation include, but is not limited to, atorvastatin, simvastatin, pravastatin, cerivastatin, mevastatin (see U.S. Pat. No. 3,883,140, the entire disclosure is herein incorporated by reference), velostatin (also called synvinolin; see U.S. Pat. Nos. 4,448,784 and 4,450,171 these entire disclosures are herein incorporated by reference), fluvastatin, lovastatin, rosuvastatin and fluindostatin (Sandoz XU-62-320), dalvastain (EP Appln. Pubin. No. 738510 A2, the entire disclosure is herein incorporated by reference), eptastatin, pitavastatin, or pharmaceutically acceptable salts thereof or a combination thereof. In various embodiments, the statin may comprise mixtures of (+)R and (−)-S enantiomers of the statin. In various embodiments, the statin may comprise a 1:1 racemic mixture of the statin.

Anti-inflammatory agents also include those with anti-inflammatory properties, such as, for example, amitriptyline, carbamazepine, gabapentin, pregabalin, clonidine, or a combination thereof.

Unless otherwise specified or apparent from context, where this specification and the set of claims that follows refer to an anti-inflammatory agent, the inventors are also referring to a pharmaceutically acceptable salt of the anti-inflammatory agent including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Similarly, when referring to an analgesic agent, unless otherwise specified or apparent from context, it is understood that the inventor is also referring to pharmaceutically acceptable salts including stereoisomers. Pharmaceutically acceptable salts include those salt-forming acids and bases that do not substantially increase the toxicity of the compound. Some examples of potentially suitable salts include salts of alkali metals such as magnesium, calcium, sodium, potassium and ammonium, salts of mineral acids such as hydrochloric, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

A "drug depot" is the composition in which at least one anti-inflammatory agent and at least one analgesic agent or the pharmaceutically acceptable salts of either or both are administered to the body. Thus, a drug depot may comprise a physical structure to facilitate implantation and retention in a desired site (e.g., nasal cavity, sinus cavity, cardiac site of the patient, particularly at or near a site of surgery, or other site of inflammation, etc.). The drug depot also comprises the drug itself. The term "drug" as used herein is generally meant to refer to any substance that alters the physiology of a patient. The term "drug" may be used interchangeably herein with the terms "therapeutic agent," "therapeutically effective amount," and "active pharmaceutical ingredient" or "API." It will be understood that unless otherwise specified a "drug" formulation may include more than one therapeutic agent, wherein exemplary combinations of therapeutic agents include a combination of two or more drugs. The drug provides a concentration gradient of the therapeutic agent for delivery to the site. In various embodiments, the drug depot provides an optimal drug concentration gradient of the therapeutic agent at a distance of up to about 0.1 cm to about 5 cm from the implant site (e.g., within the nasal and/or sinus cavity or at or near cardiac tissue), and comprises at least one anti-inflammatory agent or its pharmaceutically acceptable salt and/or at least one analgesic agent or its pharmaceutically acceptable salt.

A "depot" includes but is not limited to capsules, microspheres, microparticles; microcapsules, microfibers particles, nanospheres, nanoparticles, coating, matrices, wafers, film, strip, ribbon, sponge, patch, pills, pellets, emulsions, liposomes, micelles, gels, or other pharmaceutical delivery compositions or a combination thereof. The drug depot may comprise a pump that holds and administers the pharmaceutical (e.g., anti-inflammatory and/or analgesic). In some embodiments, the drug depot has pores that allow release of the drug from the depot. The drug depot will allow fluid in the depot to displace the drug. However, cell infiltration into the depot will be prevented by the size of the pores of the depot. In this way, in some embodiments, the depot should not function as a tissue scaffold and allow tissue growth. Rather, the drug depot will solely be utilized for drug delivery. In some embodiments, the pores in the drug depot will be less than 250 to 500 microns. This pore size will prevent cells from infiltrating the drug depot and laying down scaffolding cells. Thus, in this embodiment, drug will elute from the drug depot as fluid enters the drug depot, but cells will be prevented from entering. In some embodiments, where there are little or no pores, the drug will elute out from the drug depot by the action of enzymes, by hydrolytic action and/or by other similar mechanisms in the human body.

Suitable drug depots for use in the present application are described in U.S. Provisional Application No. 61/046,246 filed Apr. 18, 2008, U.S. Provisional Application No. 61/046,218 filed Apr. 18, 2008, U.S. Provisional Application No. 61/046,218 filed Apr. 18, 2008, U.S. Provisional Application No. 61/046,201 filed Apr. 18, 2008, U.S. Ser. No. 12/105,864 filed Apr. 18, 2008 and U.S. Ser. No. 12/105,375 filed Apr. 18, 2008. The entire disclosure of these applications is herein incorporated by reference into the present application.

Suitable materials for the depot are ideally pharmaceutically acceptable biodegradable and/or any bioabsorbable materials that are preferably FDA approved or GRAS materials. These materials can be polymeric or non-polymeric, as well as synthetic or naturally occurring, or a combination thereof. In various embodiments, the drug depot may not be biodegradable or comprise material that is not biodegradable. Non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers or combinations thereof.

The drug depot may comprise non-resorbable polymers as well. These non-resorbable polymers can include, but are not limited to, delrin, polyurethane, copolymers of silicone and polyurethane, polyolefins (such as polyisobutylene and polyisoprene), acrylamides (such as polyacrylic acid and poly(acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. Typically, the non-degradable drug depots may need to be removed.

A "therapeutically effective amount" or "effective amount" is such that when administered, the drug results in alteration of the biological activity, such as, for example, inhibition of inflammation, reduction or alleviation of pain, improvement in the condition through the reduction in edema etc. The dosage administered to a patient can unless otherwise specified or apparent from context be as single or multiple doses depending upon a variety of factors, including the drug's administered pharmacokinetic properties, the route of administration, patient conditions and characteristics (sex, age, body weight, health, size, etc.), extent of symptoms, concurrent treatments, frequency of treatment and the effect desired. In some embodiments, because the analgesic and/or anti-inflammatory agent is locally administered, therapeutically effective doses may be less than doses administered by other routes (oral, topical, etc.). For example, the drug dose delivered from the drug depot may be, for example, 10%, 20%, 30%, 40%, 50%, 60%, 70%, 80%, 90%, 95%, 99%, or 99.9% less than the oral dosage or injectable dose. In turn, systemic side effects, such as for example, liver transaminase elevations, hepatitis, liver failure, myopathy, constipation, etc. may be reduced or eliminated.

In some embodiments the depot is designed for immediate release. In other embodiments the drug depot is designed for sustained release. In other embodiments, the drug depot comprises one or more immediate release surfaces and one or more sustain release surfaces.

The phrases "sustained release" or "sustain release" (also referred to as extended release or controlled release) are used herein to refer to one or more therapeutic agent(s) that is introduced into the body of a human or other mammal and continuously or continually releases a stream of one or more therapeutic agents over a predetermined time period and at a therapeutic level sufficient to achieve a desired therapeutic effect throughout the predetermined time period (e.g., certain dose/per day). Reference to a continuous or continual release stream is intended to encompass release that occurs as the result of biodegradation in vivo of the drug depot, or a matrix or component thereof, or as the result of metabolic transformation or dissolution of the therapeutic agent(s) or conjugates of therapeutic agent(s). As persons of ordinary skill are aware, sustained release formulations may, by way of example, be created as films, slabs, strip, fibers, sponges, or gels. In some embodiments, microparticles, microspheres, microcapsules, spheroids, shaped derivatives or pastes are disposed in the film or sponge. The formulations may be in a form that is suitable for suspension in isotonic saline, physiological buffer or other solution acceptable for injection into a patient. Further, the formulations may be used in conjunction with any implantable, insertable or injectable system that a person of ordinary skill would appreciate as useful in connection with embodiments herein including but not limited to parenteral formulations, microspheres, microcapsules, gels, pastes, implantable rods, pellets, films, strips, plates or fibers, etc.

The phrase "immediate release" is used herein to refer to one or more therapeutic agent(s) that is introduced into the body and that is allowed to dissolve in or become absorbed at the location to which it is administered, with no intention of delaying or prolonging the dissolution or absorption of the drug. Immediate release refers to the release of drug within a short time period following administration, e.g., generally within a few minutes to about 1 hour.

The term "mammal" refers to organisms from the taxonomy class "mammalian," including but not limited to humans, other primates such as chimpanzees, apes, orangutans and monkeys, rats, mice, cats, dogs, cows, horses, etc. In various embodiments, the mammal is a human patient.

The phrase "release rate profile" refers to the percentage of active ingredient that is released over fixed units of time, e.g., mcg/hr, mcg/day, mg/hr, mg/day, 10% per day for ten days, etc. As persons of ordinary skill know, a release rate profile may be but need not be linear. By way of a non-limiting example, the drug depot may be in a film or strip or patch form that releases at least one analgesic agent and at least one anti-inflammatory agent over a period of time.

Treating or treatment of a disease or condition (e.g., pain and/or inflammation) refers to executing a protocol, which may include administering one or more drugs to a patient (human, normal or otherwise, or other mammal), in an effort to alleviate signs or symptoms of the disease. Alleviation can occur prior to signs or symptoms of the disease or condition appearing, as well as after their appearance. Thus, "treating" or "treatment" includes "preventing" or "prevention" of disease or undesirable condition (e.g., pain and/or inflammation). In addition, "treating" or "treatment" does not require complete alleviation of signs or symptoms, does not require a cure, and specifically includes protocols that have only a marginal effect on the patient. "Reducing pain and/or inflammation" includes a decrease in pain and/or inflammation and does not require complete alleviation of pain and/or inflammation signs or symptoms, and does not require a cure. In various embodiments, reducing pain and/or inflammation includes even a marginal decrease in pain and/or inflammation. By way of example, the administration of the effective dosages of at least one analgesic agent and at least one anti-inflammatory agent may be used to prevent, treat or relieve the symptoms of pain and/or inflammation for different diseases or conditions. These diseases/conditions may comprise chronic inflammatory diseases, including, but not limited to sinusitis, (acute and chronic), rhinitis, nasal and or sinus infection, nasal and/or sinus surgery, epitaxis (nose bleeds), sinus bleeding, nasal and/or sinus obstruction, nasal and/or sinus polyps, nasal and/or sinus cancer, nasal and/or sinus trauma. The drug depot may be used to treat, prevent or reduce diseases/conditions, such as cardiovascular disease. Cardiovascular disease (CVD) is a general term used to classify numerous conditions that affect the heart, heart valves, blood, and vasculature of the body. Cardiovascular diseases include coronary artery disease, angina pectoris, myocardial infarction, atherosclerosis, congestive heart failure, hypertension, cerebrovascular disease, stroke, transient ischemic attacks, cardiomyopathy, arrhythmias, aortic stenosis, or aneurysm.

"Localized" delivery includes delivery where one or more drugs are deposited at or near or within a tissue, for example, within the nasal or sinus cavities or cardiac tissue or in close proximity (e.g., within about 5 cm, or preferably within 0.1 cm) thereto. A "targeted delivery system" provides delivery of one or more drugs depots, gels or depot dispersed in the gel having a quantity of therapeutic agent that can be deposited at or near the target site (e.g., nasal or sinus cavity or cardiac tissue) as needed for treatment of pain, inflammation or other disease or condition.

The term "biodegradable" includes that all or parts of the drug depot will degrade over time by the action of enzymes, by hydrolytic action and/or by other similar mechanisms in the human body. In various embodiments, "biodegradable" includes that the depot (e.g., strip, film, sheet, etc.) can break down or degrade within the body to non-toxic components after or while a therapeutic agent has been or is being released. By "bioerodible" it is meant that the depot will erode or degrade over time due, at least in part, to contact with substances found in the surrounding tissue, fluids or by cellular action. By "bioabsorbable" it is meant that the depot will be broken down and absorbed within the human body, for example, by a cell or tissue. "Biocompatible" means that the depot will not cause substantial tissue irritation or necrosis at the target tissue site.

The phrase "pain management medication" includes one or more therapeutic agents that are administered to prevent, alleviate or remove pain entirely. These therapeutic agents include anti-inflammatory agents, muscle relaxants, analgesics, anesthetics, narcotics, and so forth, and combinations thereof.

In various embodiments, the depot (e.g., strip, film, patch, sponge) can be designed to cause an initial burst dose of therapeutic agent within the first 24 hours, 2 days, 3 days, 4 days, or 5 days after implantation. "Initial burst" or "burst effect" or "bolus dose" refer to the release of therapeutic agent from the depot during the first 24 hours, 2 days, 3 days, 4 days, or 5 days after the depot comes in contact with an aqueous fluid (e.g., synovial fluid, cerebral spinal fluid, etc.). This burst effect is particularly beneficial for the analgesic, while in various embodiments, for the anti-inflammatory agent a more linear release of a longer duration may be desired. The "burst effect" is believed to be due to the increased release of therapeutic agent from the depot. In alternative embodiments, the depot (e.g., gel) is designed to avoid this initial burst effect.

The drug depot comprising at least one analgesic agent or its pharmaceutically acceptable salt and/or at least one anti-inflammatory agent or its pharmaceutically acceptable salt may be co-administered with a muscle relaxant. Co-administration may involve administering at the same time in separate drug depots or formulating together in the same drug depot.

Exemplary muscle relaxants include by way of example and not limitation, alcuronium chloride, atracurium bescylate, baclofen, carbolonium, carisoprodol, chlorphenesin carbamate, chlorzoxazone, cyclobenzaprine, dantrolene, decamethonium bromide, fazadinium, gallamine triethiodide, hexafluorenium, meladrazine, mephensin, metaxalone, methocarbamol, metocurine iodide, pancuronium, pridinol mesylate, styramate, suxamethonium, suxethonium, thiocolchicoside, tizanidine, tolperisone, tubocuarine, vecuronium, or combinations thereof.

The drug depot may also comprise other therapeutic agents or active ingredients in addition to the at least one analgesic agent or its pharmaceutically acceptable salt and/ or at least one anti-inflammatory agent or its pharmaceutically acceptable salt. Suitable additional therapeutic agents include, but are not limited to, integrin antagonists, alpha-4 beta-7 integrin antagonists, cell adhesion inhibitors, interferon gamma antagonists, CTLA4-Ig agonists/antagonists (BMS-188667), CD40 ligand antagonists, Humanized anti-IL-6 mAb (MRA, Tocilizumab, Chugai), HMGB-1 mAb (Critical Therapeutics Inc.), anti-IL2R antibodies (daclizumab, basilicimab), ABX (anti IL-8 antibodies), recombinant human IL-10, or HuMax IL-15 (anti-IL 15 antibodies).

Other suitable therapeutic agents that may be co-administered with the anti-inflammatory agent and/or analgesic agent include IL-1 inhibitors, such Kineret® (anakinra) which is a recombinant, non-glycosylated form of the human interleukin-1 receptor antagonist (IL-1Ra), or AMG 108, which is a monoclonal antibody that blocks the action of IL-1. Therapeutic agents also include excitatory amino acids such as glutamate and aspartate, antagonists or inhibitors of glutamate binding to NMDA receptors, AMPA receptors, and/or kainate receptors. It is contemplated that where desirable a pegylated form of the above may be used. Examples of other therapeutic agents include NF kappa B inhibitors such as glucocorticoids, antioxidants, such as dithiocarbamate.

Specific examples of additional therapeutic agents suitable for use include, but are not limited to, an anabolic growth factor or anti-catabolic growth factor, analgesic agent, or an osteoinductive growth factor or a combination thereof.

Suitable anabolic growth or anti-catabolic growth factors include, but are not limited to, a bone morphogenetic protein, a growth differentiation factor, a LIM mineralization protein, CDMP or progenitor cells or a combination thereof.

Suitable analgesic agents include, but are not limited to, acetaminophen, bupivacaine, opioid analgesics such as amitriptyline, carbamazepine, gabapentin, pregabalin, clonidine, opioid analgesics or a combination thereof. Opioid analgesics include, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, papaveretum, pentazocine, phenadoxone, phenomorphan, phenazocine, phenoperidine, piminodine, piritramide, propheptazine, promedol, properidine, propoxyphene, sufentanil, tilidine, tramadol or a combination thereof.

For each anti-inflammatory agent and/or analgesic agent, in some embodiments, the release of each compound may be for at least one, at least two, at least three, at least four, at least five, at least six, at least seven, at least eight, at least nine, at least ten, at least eleven, at least twelve, at least thirteen, at least fourteen, or at least fifteen days, or longer.

The therapeutic agent also includes its pharmaceutically acceptable salt. As used herein, "pharmaceutically acceptable salts" refer to derivatives of the disclosed compounds (e.g., esters or amines) wherein the parent compound may be modified by making acidic or basic salts thereof. Examples of pharmaceutically acceptable salts include, but are not limited to, mineral or organic acid salts of basic residues such as amines; alkali or organic salts of acidic residues such as carboxylic acids. The pharmaceutically acceptable salts include the conventional non-toxic salts or, the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, or nitric acids; or the salts prepared from organic acids such as acetic, fuoric, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, tolunesulfonic, methanesulfonic, ethane disulfonic, oxalic, isethionic acid. Pharmaceutically acceptable also includes the racemic mixtures ((+)-R and (−)-S enantiomers) or each of the dextro and levo isomers of the therapeutic agent individually. The therapeutic agent may be in the free acid or base form or be pegylated for long acting activity.

Sulfazalazine

In one embodiment, the anti-inflammatory agent in the drug depot comprises sulfasalazine. Sulfasalazine is also known as 6-oxo-3-((4-(pyridin-2-ylsulfamoyl)phenyl) hydrazinylidene]cyclohexa-1,4-diene-1-carboxylic acid. Sulfasalazine or a pharmaceutically acceptable salt thereof is available from various pharmaceutical manufacturers. In one embodiment, the dosage of sulfasalazine is from approximately 0.005 µg/day to approximately 3000 mg/day. Additional dosages of sulfasalazine include from approximately 0.005 µg/day to approximately 2000 mg/day; approximately 0.005 µg/day to approximately 1000 mg/day; approximately 0.005 µg/day to approximately 100 mg/day; approximately 0.005 µg/day to approximately 1 mg/day; approximately 0.005 µg/day to approximately 80 µg/day; approximately 0.01 to approximately 70 µg/day; approximately 0.01 to approximately 65 µg/day; approximately 0.01 to approximately 60 µg/day; approximately 0.01 to approximately 55 µg/day; approximately 0.01 to approximately 50 µg/day; approximately 0.01 to approximately 45 µg/day; approximately 0.01 to approximately 40 µg/day; approximately 0.025 to approximately 35 µg/day; approximately 0.025 to approximately 30 µg/day; approximately 0.025 to approximately 25 µg/day; approximately 0.025 to approximately 20 µg/day; and approximately 0.025 to approximately 15 µg/day. In another embodiment, the dosage of sulfasalazine is from approximately 0.05 to approximately 15 µg/day. In another embodiment, the dosage of sulfasalazine is from approximately 0.05 to approximately 10 pig/day.

Sulindac

In one embodiment, the anti-inflammatory agent in the drug depot comprises sulindac. Sulindac, also known as 2-[6-fluoro-2-methyl-3-[(4-methylsulfinylphenyl)-methyl-idene]inden-1-yl]-acetic acid may be represented by the formula $C_{20}H_{17}FO_3S$. Sulindac or a pharmaceutically acceptable salt thereof is available from various pharmaceutical manufacturers.

The dosage of sulindac may be from approximately 0.001 µg/day to approximately 400 mg/day. Additional dosages of sulindac include from approximately 0.001 µg/day to approximately 200 mg/day; approximately 0.001 µg/day to approximately 100 mg/day; approximately 0.001 µg/day to approximately 1 mg/day; approximately 0.001 to approximately 500 µg/day; approximately 0.001 to approximately 100 µg/day; approximately 0.025 to approximately 75 mg/day; approximately 0.025 to approximately 65 µg/day; approximately 0.025 to approximately 60 µg/day; approximately 0.025 to approximately 55 µg/day; approximately 0.025 to approximately 50 µg/day; approximately 0.025 to approximately 45 µg/day; approximately 0.025 to approximately 40 µg/day; approximately 0.025 to approximately 35 µg/day; approximately 0.005 to approximately 30 µg/day; approximately 0.005 to approximately 25 µg/day; approximately 0.005 to approximately 20 µg/day; and approximately 0.005 to approximately 15 µg/day. In another embodiment, the dosage of sulindac is from approximately 0.01 to approximately 15 µg/day. In another embodiment, the dosage of sulindac is from approximately 0.01 to approximately 10 µg/day. In another embodiment, the dosage of sulindac is from approximately 0.01 to approximately 5 µg/day. In another embodiment, the dosage of sulindac is from approximately 0.01 to approximately 20 µg/day. In another embodiment, the sulindac is administered in a drug depot that releases 9.6 µg/day.

Clonidine

In one embodiment, the anti-inflammatory agent in the depot is clonidine, also referred to as 2,6-dichloro-N-2-imidazolidinyldenebenzenamine. Clonidine or a pharmaceutically acceptable salt thereof is available from various pharmaceutical manufactures.

The dosage may be from approximately 0.0005 to approximately 960 µg/day. Additional dosages of clonidine include from approximately 0.0005 to approximately 900 µg/day; approximately 0.0005 to approximately 500 µg/day; approximately 0.0005 to approximately 250 µg/day; approximately 0.0005 to approximately 100 µg/day; approximately 0.0005 to approximately 75 µg/day; approximately 0.001 to approximately 70 µg/day; approximately 0.001 to approximately 65 µg/day; approximately 0.001 to approximately 60 µg/day; approximately 0.001 to approximately 55 µg/day; approximately 0.001 to approximately 50 mg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; approximately 0.0025 to approximately 15 µg/day; approximately 0.0025 to approximately 10 µg/day; approximately 0.0025 to approximately 5 µg/day; and approximately 0.0025 to approximately 2.5 µg/day. In another embodiment, the dosage of clonidine is from approximately 0.005 to approximately 15 µg/day. In another embodiment, the dosage of clonidine is from approximately 0.005 to approximately 10 µg/day. In another embodiment, the dosage of clonidine is from approximately 0.005 to approximately 5 µg/day. In another embodiment, the dosage of clonidine is from approximately 0.005 to 2.5 jug/day. In some embodiments, the amount of clonidine is between 40 and 600 µg/day. In some embodiments, the amount of clonidine is between 200 and 400 µg/day.

Fluocinolone

In one embodiment, the anti-inflammatory agent in the drug depot comprises fluocinolone or a pharmaceutically acceptable salt thereof such as the acetonide salt. Fluocinolone is available from various pharmaceutical manufacturers. The dosage of fluocinolone may be from approximately 0.0005 to approximately 100 µg/day. Additional dosages of fluocinolone include from approximately 0.0005 to approximately 50 µg/day; approximately 0.0005 to approximately 25 µg/day; approximately 0.0005 to approximately 10 µg/day; approximately 0.0005 to approximately 5 µg/day; approximately 0.0005 to approximately 1 µg/day; approximately 0.0005 to approximately 0.75 µg/day; approximately 0.0005 to approximately 0.5 µg/day; approximately 0.0005 to approximately 0.25 µg/day; approximately 0.0005 to approximately 0.1 µg/day; approximately 0.0005 to approximately 0.075 µg/day; approximately 0.0005 to approximately 0.05 µg/day; approximately 0.001 to approximately 0.025 µg/day; approximately 0.001 to approximately 0.01 µg/day; approximately 0.001 to approximately 0.0075 µg/day; approximately 0.001 to approximately 0.005 µg/day; approximately 0.001 to approximately 0.025 µg/day; and approximately 0.002 µg/day. In another embodiment, the dosage of fluocinolone is from approximately 0.001 to approximately 15 µg/day. In another embodiment, the dosage of fluocinolone is from approximately 0.001 to approximately 10 µg/day. In another embodiment, the dosage of fluocinolone is from approximately 0.001 to approximately 5 µg/day. In another embodiment, the dosage of fluocinolone is from approximately 0.001 to 2.5 µg/day. In some embodiments, the amount of fluocinolone is between 40 and 600 µg/day. In some embodiments, the amount of fluocinolone is between 200 and 400 µg/day.

Dexamethasone

In one embodiment, the anti-inflammatory agent in the drug depot is dexamethasone free base or dexamethasone acetate, also referred to as 8S,9R,10S,11S,13S,14S,16R,17R)-9-Fluoro-11,17-dihydroxy-17-(2-hydroxyacetyl)-10,13,16-trimethyl-6,7,8,11,12,14,15,16 octahydrocyclopenta[a]-phenanthren-3-one), or a pharmaceutically acceptable salt thereof, which is available from various manufacturers.

In various embodiments, dexamethasone may be released from the depot at a dose of about 10 µg to about 80 mg/day, about 2.4 ng/day to about 50 mg/day, about 50 ng/day to about 2.5 mg/day, about 250 ng/day to about 250 ug/day, about 250 ng/day to about 50 ug/day, about 250 ng/day to about 25 ug/day, about 250 ng/day to about 1 ug/day, about 300 ng/day to about 750 ng/day or about 0.50 ug/day. In various embodiments, the dose may be about 0.01 to about 10 µg/day or about 1 ng to about 120 µg/day.

In one exemplary embodiment, the dexamethasone is dexamethasone sodium phosphate.

GED

In one embodiment, the therapeutic agent in the drug depot is GED (guanidinoethyldisulfide), which is an inducible nitric oxide synthase inhibitor having anti-inflammatory properties. GED may be in its hydrogen carbonate salt form.

The dosage of GED may be from approximately 0.0005 µg/day to approximately 100 mg/day. Additional dosages of GED include from approximately 0.0005 µg/day to approximately 50 mg/day; approximately 0.0005 µg/day to approximately 10 mg/day; approximately 0.0005 µg/day to approximately 1 mg/day; approximately 0.0005 to approximately 800 µg/day; approximately 0.0005 to approximately 50 µg/day; approximately 0.001 to approximately 45 µg/day; approximately 0.001 to approximately 40 µg/day; approximately 0.001 to approximately 35 µg/day; approximately 0.0025 to approximately 30 µg/day; approximately 0.0025 to approximately 25 µg/day; approximately 0.0025 to approximately 20 µg/day; and approximately 0.0025 to approximately 15 µg/day. In another embodiment, the dosage of GED is from approximately 0.005 to approximately 15 µg/day. In another embodiment, the dosage of GED is from approximately 0.005 to approximately 10 µg/day. In another embodiment, the dosage of GED is from approximately 0.005 to approximately 5 µg/day. In another embodiment, the dosage of GED is from approximately 0.005 to 2.5 µg/day. In some embodiments, the amount of GED is between 40 and 600 µg/day. In some embodiments, the amount of GED is between 200 and 400 µg/day.

In one exemplary embodiment the dosage of GED is between 0.5 and 4 mg/day. In another exemplary embodiment the dosage of GED is between 0.75 and 3.5 mg/day.

Lovastatin

In one exemplary embodiment, the anti-inflammatory agent in the depot comprises lovastatin. Lovastatin is a statin that may be obtained from various manufacturers in various forms (e.g., injection, powder, etc.). For example, lovastatin may be obtained from Merck as Mevacor® (see U.S. Pat. No. 4,231,938, the entire disclosure is herein incorporated by reference). Suitable pharmaceutically acceptable salts of lovastatin include one or more compounds derived from bases such as sodium hydroxide, potassium hydroxide, lithium hydroxide, calcium hydroxide, 1-deoxy-2-(methylamino)-D-glucitol, magnesium hydroxide, zinc hydroxide, aluminum hydroxide, ferrous or ferric hydroxide, ammonium hydroxide or organic amines such as N-methylglucamine, choline, arginine or the like or combinations thereof. Suitable pharmaceutically acceptable salts of lovastatin include lithium, calcium, hemicalcium, sodium, potassium, magnesium, aluminum, ferrous or ferric salts thereof or a combination thereof.

In various embodiments, the therapeutically effective amount of lovastatin comprises from about 0.1 pg to about 2000 mg, for example, 0.1 ng to 1000 mg, 500 mg, 100 mg, 50 mg, 25 mg, 10 mg, 1 mg, 50 µg, 25 µg, 10 µg, 1 µs, 500 ng, 250 ng, 100 ng, 75 ng, 50 ng, 25 ng, 15 ng, 10 ng, 5 ng, or 1 ng of lovastatin per day. In various embodiments, the dosage may be, for example from about 3 ng/day to 0.3 µg/day.

Morphine

In one embodiment of the present invention, the analgesic agent in the drug depot is morphine. Morphine is also referred to as (5α,6α)-7,8-didehydro-4,5-epoxy-17-methyl-morphinan-3,6-diol and has the chemical formula $C_{17}H_{19}NO_3$. Morphine or a pharmaceutically acceptable salt thereof is available from various manufacturers. In one exemplary embodiment, the morphine comprises morphine sulfate or hydrochloride.

The dosage of the morphine may be from 0.1 mg to 1000 mg per day. For example, the dosage of morphine may be for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 120 mg, 130 mg, 140 mg, 150 mg, 160 mg, 170 mg, 180 mg, 190 mg, 200 mg of morphine per day.

Tramadol

In one embodiment, the analgesic agent in the drug depot is tramadol. Tramadol is also referred to as (±)cis-2-[(dimethylamino)methyl]-1-(3-methoxyphenyl) cyclohexanol hydrochloride and has the chemical formula $C_{16}H_{25}NO_2$. Tramadol or a pharmaceutically acceptable salt thereof is available from various manufacturers. In various embodiments, tramadol HCL was used.

The dosage of the tramadol may be from 0.01 mg to 500 mg per day. For example, the dosage of tramadol may be for example, 0.1 mg to 2 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 75 mg, 80 mg, 85 mg, 90 mg, 95 mg, 100 mg, 120 mg, 130 mg, 140 mg, 150 mg, 160 mg, 170 mg, 180 mg, 190 mg, 200 mg, or 500 mg of tramadol per day.

In one embodiment, the drug depot contains sufficient tramadol to release between 2.5 and 30 mg/kg/day. In another embodiment the drug depot contains sufficient tramadol to release between 3 and 27.5 mg/kg/day.

The at least one anti-inflammatory agent and at least one analgesic agent may also be administered with non-active ingredients. These non-active ingredients may have multifunctional purposes including the carrying, stabilizing and controlling the release of the therapeutic agent(s). The sustained release process, for example, may be by a solution-diffusion mechanism or it may be governed by an erosion-sustained process. Typically, the depot will be a solid or semi-solid formulation comprised of a biocompatible material that can be biodegradable. The term "solid" is intended to mean a rigid material, while "semi-solid" is intended to mean a material that has some degree of flexibility, thereby allowing the depot to bend and conform to the surrounding tissue requirements.

In various embodiments, the non-active ingredients will be durable within the tissue site for a period of time equal to (for biodegradable components) or greater than (for non-biodegradable components) the planned period of drug delivery. For example, the depot material may have a melting point or glass transition temperature close to or higher than body temperature, but lower than the decomposition or degradation temperature of the therapeutic agent. However, the pre-determined erosion of the depot material can also be used to provide for slow release of the loaded therapeutic agent(s).

In various embodiments, the drug depot may not be biodegradable. For example, the drug depot may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. Typically, these types of drug depots may need to be removed.

In some instance, it may be desirable to avoid having to remove the drug depot after use. In those instances, the depot may comprise a biodegradable material. There are numerous materials available for this purpose and having the characteristic of being able to breakdown or disintegrate over a prolonged period of time when positioned at or near the target tissue. As a function of the chemistry of the biodegradable material, the mechanism of the degradation process can be hydrolytical or enzymatical in nature, or both. In various embodiments, the degradation can occur either at the surface (heterogeneous or surface erosion) or uniformly throughout the drug delivery system depot (homogeneous or bulk erosion).

In various embodiments, the depot may comprise a bioabsorbable, and/or a biodegradable biopolymer that may provide immediate release, or sustained release of the at least one analgesic agent and at least one anti-inflammatory agent. Examples of suitable sustained release biopolymers include but are not limited to poly (alpha-hydroxy acids), poly (lactide-co-glycolide) (PLGA or PLG), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, -caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAM (sucrose acetate isobutyrate) or combinations thereof. As persons of ordinary skill are aware, mPEG may be used as a plasticizer for PLGA, but other polymers/excipients may be used to achieve the same effect. mPEG imparts malleability to the resulting formulations.

Where different combinations of polymers are used (bi, tri (e.g., PLGA-PEO-PLGA) or terpolymers), they may be used in different molar ratios, 1:1, 2:1, 3:1, 4:1, 5:1, 6:1, 7:1, 8:1, 9:1, or 10:1. In various embodiments, for the long release (e.g. 30 days or longer), the depot comprises 50:50 PLGA to 100 PLA. The molecular weight range is 0.45 to 0.8 dl/g.

In various embodiments, the molecular weight of the polymer can be a wide range of values. The average molecular weight of the polymer can be from about 1000 to about 10,000,000; or about 1,000 to about 1,000,000; or about 5,000 to about 500,000; or about 10,000 to about 100,000; or about 20,000 to 50,000.

In some embodiments, the at least one biodegradable polymer comprises poly(lactic-co-glycolic acid) (PLA) or poly(orthoester) (POE) or a combination thereof. The poly (lactic-co-glycolic acid) may comprise a mixture of polyglycolide (PGA) and polylactide and in some embodiments, in the mixture, there is more polylactide than polyglycolide. In various other embodiments there is 100% polylactide and 0% polyglycolide; 95% polylactide and 5% polyglycolide; 90% polylactide and 10% polyglycolide; 85% polylactide and 15% polyglycolide; 80% polylactide and 20% polyglycolide; 75% polylactide and 25% polyglycolide; 70% polylactide and 30% polyglycolide; 65% polylactide and 35% polyglycolide; 60% polylactide and 40% polyglycolide; 55% polylactide and 45% polyglycolide; 50% polylactide and 50% polyglycolide; 45% polylactide and 55% polyglycolide; 40% polylactide and 60% polyglycolide; 35% polylactide and 65% polyglycolide; 30% polylactide and 70% polyglycolide; 25% polylactide and 75% polyglycolide; 20% polylactide and 80% polyglycolide; 15% polylactide and 85% polyglycolide; 10% polylactide and 90% polyglycolide; 5% polylactide and 95% polyglycolide; and 0% polylactide and 100% polyglycolide.

In various embodiments that comprise both polylactide and polyglycolide; there is at least 95% polylactide; at least 90% polylactide; at least 85% polylactide; at least 80% polylactide; at least 75% polylactide; at least 70% polylactide; at least 65% polylactide; at least 60% polylactide; at least 55%; at least 50% polylactide; at least 45% polylactide; at least 40% polylactide; at least 35% polylactide; at least 30% polylactide; at least 25% polylactide; at least 20% polylactide; at least 15% polylactide; at least 10% polylactide; or at least 5% polylactide; and the remainder of the biopolymer being polyglycolide.

In various embodiments, the drug depot comprises poly (lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone, glycolide-caprolactone or a combination thereof.

As persons of ordinary skill in the art are aware, implantable elastomeric depot compositions having a blend of polymers with different end groups are used the resulting formulation will have a lower burst index and a regulated duration of delivery. For example, one may use polymers with acid (e.g., carboxylic acid) and ester end groups (e.g., lauryl, methyl or ethyl ester end groups).

Additionally, by varying the comonomer ratio of the various monomers that form a polymer (e.g., the L/G/CL (CL refers to caprolactone, G refers to glycolic acid and L refers to lactic acid) or G/CL ratio for a given polymer) there will be a resulting depot composition having a regulated burst index and duration of delivery. For example, a depot composition having a polymer with a L/G ratio of 50:50 may have a shoat duration of delivery ranging from about two days to about one month; a depot composition having a polymer with a L/G ratio of 65:35 may have a duration of delivery of about two months; a depot composition having a polymer with a L/G ratio of 75:25 or L/CL ratio of 75:25 may have a duration of delivery of about three months to about four months; a depot composition having a polymer ratio with a L/G ratio of 85:15 may have a duration of delivery of about five months; a depot composition having a polymer with a L/CL ratio of 25:75 or PLA may have a duration of delivery greater than or equal to six months; a depot composition having a terpolymer of CL/G/L with G greater than 50% and L greater than 10% may have a duration of delivery of about one month and a depot composition having a terpolymer of CL/G/L with G less than 50% and L less than 10% may have a duration months up to six months. In general, increasing the G content relative to the CL content shortens the duration of delivery whereas increasing the CL content relative to the G content lengthens the duration of delivery.

In some embodiments, the biodegradable polymer comprises at least 10 wt %, at least 50 wt. %, at least 60 wt. %, at least 70 wt. %, at least 80 wt. %, at least 85 wt. %, at least 90 wt. %, at least 95 wt. %, or at least 99 wt. % of the formulation. In some embodiments, the at least one biodegradable polymer and the analgesic and the anti-inflammatory are the only components of the pharmaceutical formulation.

In some embodiments, at least 75% of the particles have a size from about 1 micrometer to about 200 micrometers. In some embodiments, at least 85% of the particles have a size from about 1 micrometer to about 100 micrometers. In some embodiments, at least 95% of the particles have a size from about 5 micrometer to about 30 micrometers. In some embodiments, all of the particles have a size from about 10 micrometer to about 30 micrometers.

In some embodiments, at least 75% of the particles have a size from about 5 micrometer to about 20 micrometers. In some embodiments, at least 85% of the particles have a size from about 5 micrometers to about 20 micrometers. In some embodiments, at least 95% of the particles have a size from about 5 micrometer to about 20 micrometers. In some embodiments, all of the particles have a size from about 5 micrometer to about 20 micrometers.

The depot may optionally contain inactive materials such as buffering agents and pH adjusting agents such as potassium bicarbonate, potassium carbonate, potassium hydroxide, sodium acetate, sodium borate, sodium bicarbonate, sodium carbonate, sodium hydroxide or sodium phosphate; degradation/release modifiers; drug release adjusting agents; emulsifiers; preservatives such as benzalkonium chloride, chlorobutanol, phenylmercuric acetate and phenylmercuric nitrate, sodium bisulfite, sodium bisulfate, sodium thiosulfate, thimerosal, methylparaben, polyvinyl alcohol and phenylethyl alcohol; solubility adjusting agents; stabilizers; and/or cohesion modifiers. Typically, any such inactive materials will be present within the range of 0-75 wt %, and more typically within the range of 0-30 wt %. If the depot is to be placed at or near cardiac tissue, in various embodiments, the depot may comprise sterile preservative free material.

The depot can be different sizes, shapes and configurations. There are several factors that can be taken into consideration in determining the size, shape and configuration of the drug depot. For example, both the size and shape may allow for ease in positioning the drug depot at the target tissue site that is selected as the implantation or injection site. In addition, the shape and size of the system should be selected so as to minimize or prevent the drug depot from moving after implantation or injection. In various embodiments, the drug depot can be shaped like a flat surface such as a disc, film, strip or sheet or the like. Flexibility may be a consideration so as to facilitate placement of the drug depot. In various embodiments, the drug depot can be different sizes, for example, the drug depot may be a length of from about 0.5 mm to 5 mm and have a diameter of from about 0.01 to about 2 mm. In various embodiments, the drug depot may have a layer thickness of from about 0.005 to 1.0 mm, such as, for example, from 0.05 to 0.75 mm.

In various embodiments, the drug depot may be in the form of a film, patch or strip and may have a thickness of about 500 microns to about 5,000 microns or in some embodiments about 0.1 mm to about 3 mm or in some embodiments about 0.1 mils to about 60 mils.

In various embodiments, when the drug depot comprises a film or strip, it may be placed at the incision site before the site is closed. The film or strip may for example be made of thermoplastic materials. Additionally, specific materials that may be advantageous for use in the film or strip include but are not limited to the compounds identified above as sustained release biopolymers. The drug depot may be formed by mixing the at least one analgesic agent and the at least one anti-inflammatory agent with the polymer.

Radiographic markers can be included on the drug depot to permit the user to position the depot accurately into the target site of the patient. These radiographic markers will also permit the user to track movement and degradation of the depot at the site over time. In this embodiment, the user may accurately position the depot in the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles. In various embodiments, the radiographic marker could be a spherical shape or a ring around the depot.

Packing

The drug depot can be part of a packing material or several drug depots can placed on or around each other until the target area is packed. The packing material, among other things, can act as a hemostatic agent and absorb bodily fluid and/or blood during or after surgery. Packing material includes cellulose based materials, such as cellulose gauze made from cotton or regenerated cellulose fiber, regenerated cellulose sponge, other cellulose fibers or the like can be utilized to absorb body fluids and blood during surgery. The packing material can also contain thrombin, chitin, chitosan, fibrin, amorphous fumed silica, gelatin, corn starch, collagen, polyethylene film, polyvinyl acetate, ethylene-vinyl acetate copolymers, metal foils, laminates of cloth or paper, or a plastic film such as for example, resin-like polyethylene, vinyl acetate homopolymers, and ethylene-vinyl acetate, polypropylene, polyesters, PVC, polysaccharides, hyaluronic acid, xanthan, galactomannan, alginate, nonwoven fabrics, or the like.

Preferably, the packing material reduces risk of contamination or infection and reduces the risk of interfering with the wound healing process and hinder the prompt recovery of the patient.

Typically, packing involves the application of packing material, such as for example, gauze, gel, cotton balls, cotton wedges, sponge, or the like to the target tissue site (e.g., nasal and/or sinus cavity, or cardiac tissue). The drug depot may be placed at or near the target tissue site alone or several drug depots can be packed at the target tissue site. Alternatively, the drug depot can be placed at the target tissue site and be packed in by the packing material (e.g., gauze, gel, cotton balls, cotton wedges, etc.) so that the drug depot remains at or near the target tissue site. In this way the packing material reduces or prevents the drug depot from migrating away from the implant site prior to surgical closure. The drug depot will release the therapeutic agent locally at the site of implantation.

The packing material may be coated with a therapeutic agent (e.g., antibiotics, petrolatum, etc.). For nasal packings, the packing material can be placed into the nose one layer at a time, folding one layer on top of the other until the area is completely packed. Often the end of the nose may be taped to keep the packing material in place or to prevent the patient from pulling it out. The packing material may be left at the site or degrade over time or it may be removed within 24-48 hours following surgery. Alternatively the packing material can abut firm tissue so that tape is not needed. For example, turbinates are folds of tissue on the insides of the nose. The folds are sufficiently firm to support packing. A piece of gauze or cotton is wedged with the drug depot (e.g., film, strip, etc.) in between the turbinates where the drug depot will release the therapeutic agent in the adjacent blood vessels.

FIG. 1A illustrates a magnified top view of one embodiment of the implantable drug depot in the form of a film or strip 10 that has the analgesic and/or an anti-inflammatory agent 12 disposed on or in the film or strip. As the drug depot degrades over time, the therapeutic agent (e.g., analgesic and/or anti-inflammatory) is released locally to the site of implantation.

Figure 1B:
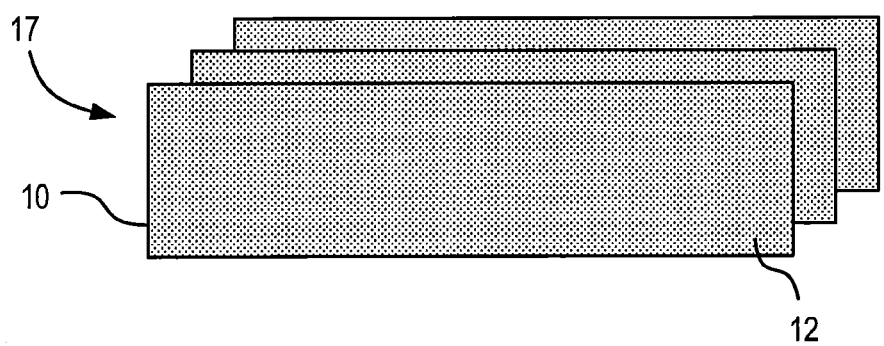
FIG. 1B illustrates a magnified top view of one embodiment of the implantable drug depot in the form of multiple films or strips that have the analgesic and/or an anti-inflammatory agent disposed on or in the films or strips. The films or strips are shown stacked together and can be used as packing material to pack at or near a cardiac tissue or within the nasal or sinus cavity.

FIG. 1B illustrates a magnified top view of one embodiment of the implantable drug depot in the form of a multiple films or strips 10 that are stacked shown as 17 one on each other that have the analgesic and/or an anti-inflammatory agent 12 disposed on or in the film or strip. The films or strips are shown stacked together and can be used as packing material at or near a cardiac tissue or within the nasal or sinus cavity.

Figure 2:
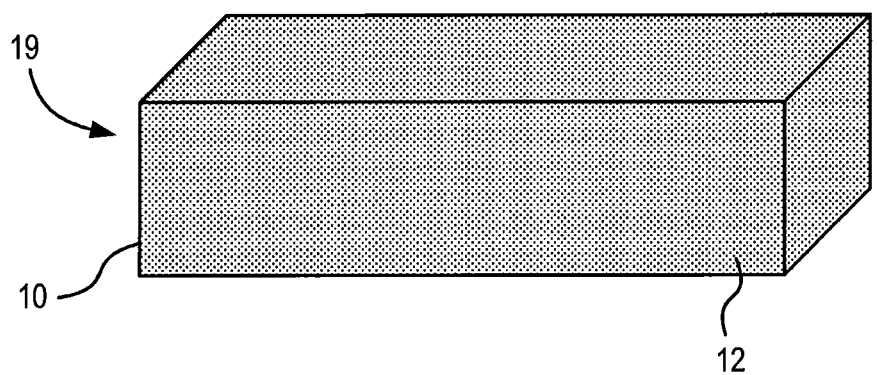
FIG. 2 illustrates a magnified side view of one embodiment of the implantable drug depot in the form of a sponge that has the analgesic and/or an anti-inflammatory agent disposed on or in the sponge.

FIG. 2 illustrates a magnified side view of one embodiment of the implantable drug depot 10 in the form of a sponge 19 that has the analgesic and/or an anti-inflammatory agent 12 disposed on or in the sponge. As the drug depot degrades over time, the therapeutic agent (e.g., analgesic and/or anti-inflammatory) is released locally to the site of implantation.

Figure 3:
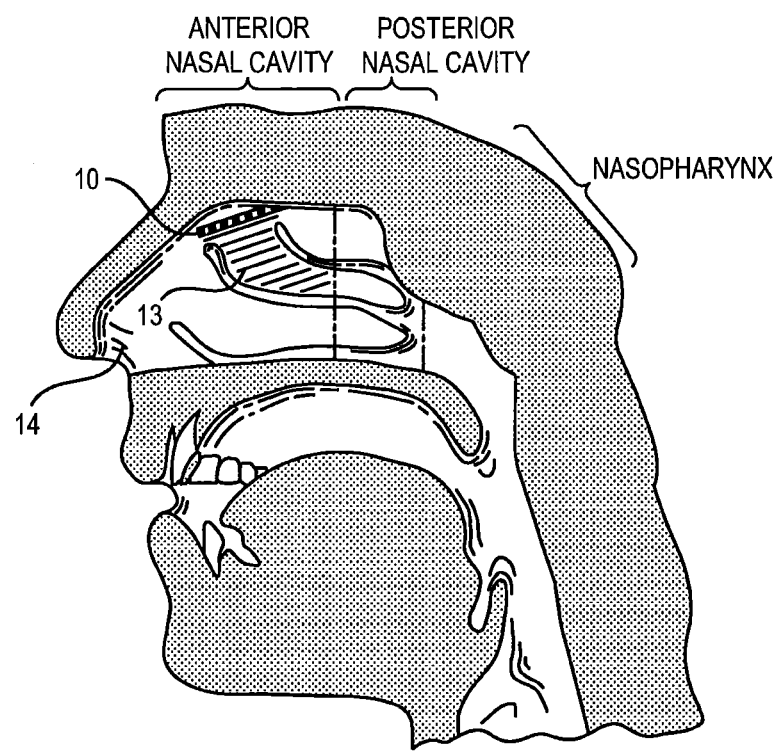
FIG. 3 illustrates a partial, side sectional view of a human head illustrating the parts of the nasal cavity with the drug depot in the form of a film or strip packing administered thereto.

FIG. 3 illustrates a partial, side sectional view of a human head illustrating the parts of the nasal cavity 14 with the drug depot in the form of a film or strip 10 on packing material 13 administered thereto. The drug depot is held in place and is packed against the anterior nasal cavity against the nasal mucosa, where the therapeutic agent can be released. The packing material holds the drug depot in position at the target tissue site.

Figure 4:
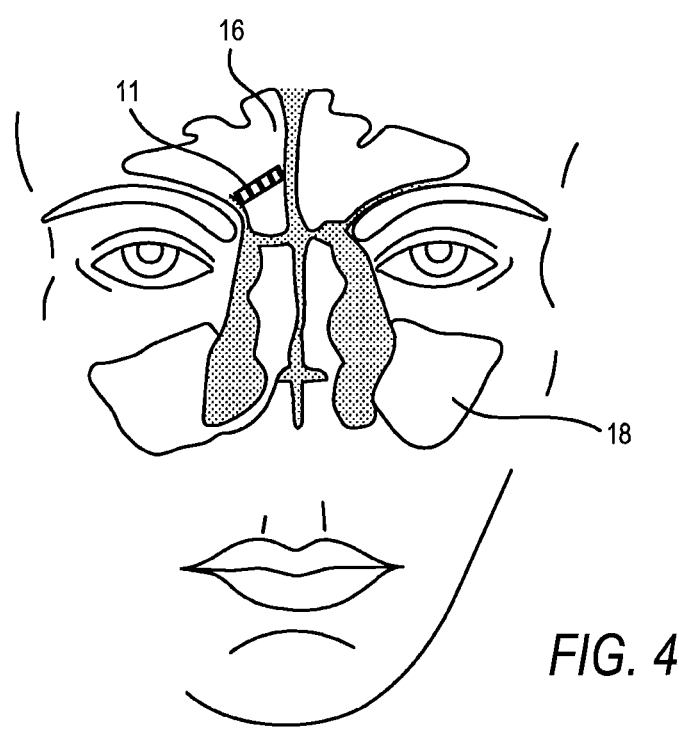
FIG. 4 illustrates a partial, front sectional view of a human head illustrating portions of a nasal cavity and sinus cavity with the drug depot in the form of a film or strip administered to the sinus frontilis.

FIG. 4 illustrates a partial, front sectional view of a human head illustrating portions of a nasal cavity and sinus cavity with the drug depot in the form of a film or strip 11 administered to the sinus frontilis 16 where the therapeutic agent can be released as the film or strip degrades. Thus, localized delivery of the therapeutic agent can be accomplished locally in the sinus cavity to prevent, treat or reduce inflammation and/or pain locally at the site of implantation. Although the sinus frontilis is shown other areas of the sinus cavity can have the drug depot implanted (e.g., sinus sphenoidalis, cellulae ethmoidalis, the sinus maximilaris 18, etc.).

Figure 5:
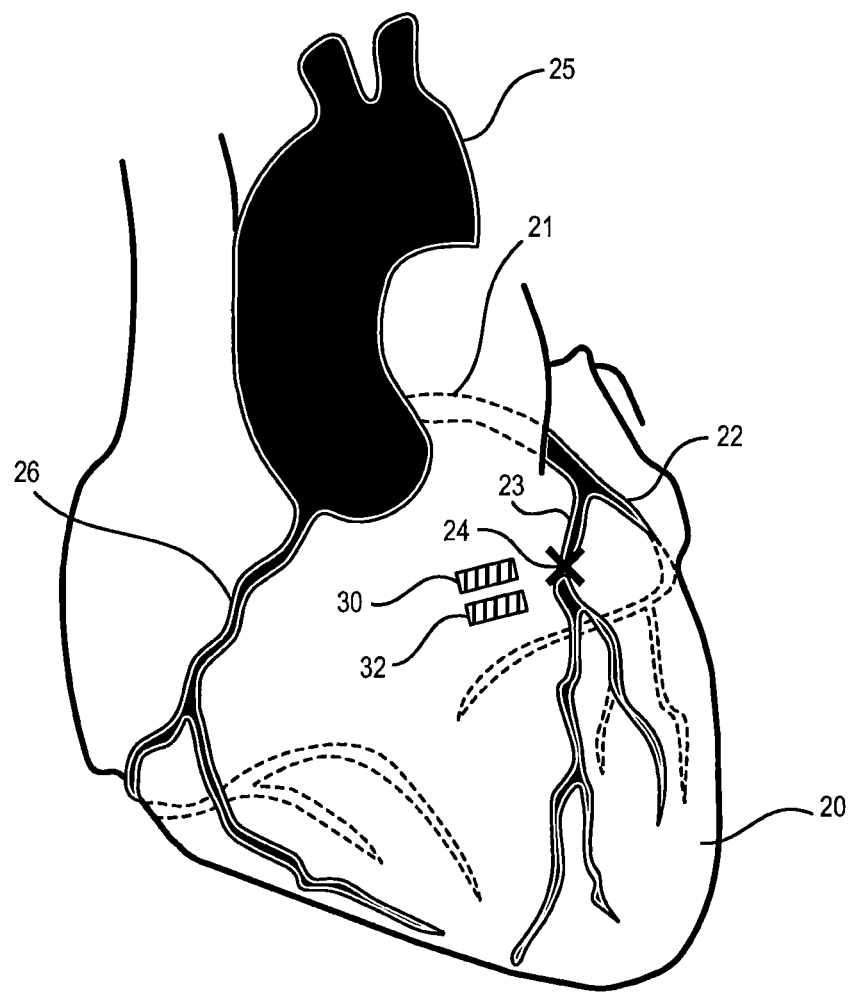
FIG. 5 schematically shows tissues and vessels of the heart where the drug depot in the form of multiple films, or strips, or cardiac patch that can be administered thereto.

Another area that is ripe with pain and/or inflammation is cardiac tissue. FIG. 5 schematically depicts the heart 20 and the target vessel, which is represented by the descending coronary artery 23 that had a surgical procedure indicated by the suture 24 after myocardial infraction. By implanting a plurality of drug depot films or strips 30 and 32 containing an anti-inflammatory or analgesic agent near the surgical site 24, edema, inflammation and/or pain can be reduced to speed the patient's recovery. Alternatively, the films or strips can be part of packing material that can absorb blood and fluid and degrade over time. The drug depot in the form of a film or strip can be placed in or around cardiac tissue. For example, the drug depot in the form of a film or strip can be placed at or near the left coronary artery 21, circumflex artery 22, aorta 25, and right coronary artery 26 or other areas at or near the heart. The drug depot may be implanted at, near or in cardiac tissue, such as for example, pericardium (e.g., serous pericardium, parietal pericardium, fibrous pericardium, visceral pericardium) myocardium, epicardium, or muscle, connective tissue at or near the heart or like tissue.

Gel

In various embodiments, the drug depot comprises a gel that can be placed at the target tissue site as a film. In various embodiments, the gel has a pre-dosed viscosity in the range of about 1 to about 500 centipoise (cps), 1 to about 200 cps, or 1 to about 100 cps. After the gel is administered to the target site, the viscosity of the gel will increase and the gel will have a modulus of elasticity (Young's modulus) in the range of about $1\times10^4$ to about $6\times10^5$ dynes/cm$^2$, or $2\times10^4$ to about $5\times10^5$ dynes/cm$^2$, or $5\times10^4$ to about $5\times10^5$ dynes/cm$^2$.

In one embodiment, a depot comprises an adherent gel comprising at least one analgesic agent and at least one anti-inflammatory agent that is evenly distributed throughout the gel. The gel may be of any suitable type, as previously indicated, and should be sufficiently viscous so as to prevent the gel from migrating from the targeted delivery site once deployed; the gel should, in effect, "stick" or adhere to the targeted tissue site. The gel may, for example, solidify upon contact with the targeted tissue or after deployment from a targeted delivery system. The targeted delivery system may be, for example, a syringe, a catheter, needle or cannula or any other suitable device. The targeted delivery system may inject the gel into or on the targeted tissue site. The therapeutic agent may be mixed into the gel prior to the gel being deployed at the targeted tissue site. In various embodiments, the gel may be part of a two-component delivery system and when the two components are mixed, a chemical process is activated to form the gel and cause it to stick or to adhere to the target tissue.

In various embodiments, a gel is provided that hardens or stiffens after delivery. Typically, hardening gel formulations may have a pre-dosed modulus of elasticity in the range of about $1\times10^4$ to about $3\times10^5$ dynes/cm$^2$, or $2\times10^4$ to about $2\times10^5$ dynes/cm$^2$, or $5\times10^4$ to about $1\times10^5$ dynes/cm$^2$. The post-dosed hardening gels (after delivery) may have a rubbery consistency and have a modulus of elasticity in the range of about $1\times10^4$ to about $2\times10^6$ dynes/cm$^2$, or $1\times10^5$ to about $7\times10^5$ dynes/cm$^2$, or $2\times10^5$ to about $5\times10^5$ dynes/cm$^2$.

In various embodiments, for those gel formulations that contain a polymer, the polymer concentration may affect the rate at which the gel hardens (e.g., a gel with a higher concentration of polymer may coagulate more quickly than gels having a lower concentration of polymer). In various embodiments, when the gel hardens, the resulting matrix is solid but is also able to conform to the irregular surface of the tissue (e.g., recesses and/or projections in tissue).

The percentage of polymer present in the gel may also affect the viscosity of the polymeric composition. For example, a composition having a higher percentage by weight of polymer is typically thicker and more viscous than a composition having a lower percentage by weight of polymer. A more viscous composition tends to flow more slowly. Therefore, a composition having a lower viscosity may be preferred in some instances.

In various embodiments, the molecular weight of the gel can be varied by any one of the many methods known in the art. The choice of method to vary molecular weight is typically determined by the composition of the gel (e.g., polymer versus non-polymer). For example in various embodiments, when the gel comprises one or more polymers, the degree of polymerization can be controlled by varying the amount of polymer initiators (e.g. benzoyl peroxide), organic solvents or activator (e.g. DMPT), cross-linking agents, polymerization agent, and/or reaction time.

Suitable gel polymers may be soluble in an organic solvent. The solubility of a polymer in a solvent varies depending on the crystallinity, hydrophobicity, hydrogen-bonding and molecular weight of the polymer. Lower molecular weight polymers will normally dissolve more readily in an organic solvent than high-molecular weight polymers. A polymeric gel, which includes a high molecular weight polymer, tends to coagulate or solidify more quickly than a polymeric composition, which includes a low-molecular weight polymer. Polymeric gel formulations, which include high molecular weight polymers, also tend to have a higher solution viscosity than a polymeric gel, which include a low-molecular weight polymer.

When the gel is designed to be a flowable gel, it can vary from low viscosity, similar to that of water, to a high viscosity, similar to that of a paste, depending on the molecular weight and concentration of the polymer used in the gel. The viscosity of the gel can be varied such that the polymeric composition can be applied to a patient's tissues by any convenient technique, for example, by brushing, dripping, injecting, or painting. Different viscosities of the gel will depend on the technique used to apply the composition.

In various embodiments, the gel has an inherent viscosity (abbreviated as "I.V." and units are in deciliters/gram), which is a measure of the gel's molecular weight and degradation time (e.g., a gel with a high inherent viscosity has a higher molecular weight and longer degradation time). Typically, a gel with a high molecular weight provides a stronger film or strip and the film or strip takes more time to degrade. In contrast, a gel with a low molecular weight degrades more quickly and provides a softer film or strip. In various embodiments, the gel has a molecular weight, as shown by the inherent viscosity, from about 0.10 dL/g to about 1.2 dL/g or from about 0.10 dL/g to about 0.40 dL/g.

In various embodiments, the gel can have a viscosity of about 300 to about 5,000 centipoise (cp). In other embodiments, the gel can have a viscosity of from about 5 to about 300 cps, from about 10 cps to about 50 cps, from about 15 cps to about 75 cps at room temperature. The gel may optionally have a viscosity enhancing agent such as, for example, hydroxypropyl cellulose, hydroxypropyl methylcellulose, hydroxyethyl methylcellulose, carboxymethylcellulose and salts thereof, Carbopol, poly-(hydroxyethylmethacrylate), poly-(methoxyethylmethacrylate), poly (methoxyethoxyethyl methacrylate), polymethylmethacrylate (PMMA), methylmethacrylate (MMA), gelatin, polyvinyl alcohols, propylene glycol, PEG 200, PEG 300, PEG 400, PEG 500, PEG 600, PEG 700, PEG 800, PEG 900, PEG 1000, PEG 1450, PEG 3350, PEG 4500, PEG 8000 or combinations thereof.

In various embodiments, when a polymer is employed in the gel, the polymeric composition includes about 10 wt % to about 90 wt % or about 30 wt % to about 60 wt % of the polymer.

In various embodiments, the gel is a hydrogel made of high molecular weight biocompatible elastomeric polymers of synthetic or natural origin. A desirable property for the hydrogel to have is the ability to respond rapidly to mechanical stresses, particularly shears and loads, in the human body.

Hydrogels obtained from natural sources are particularly appealing because they are more likely to be biodegradable and biocompatible for in vivo applications. Suitable hydrogels include natural hydrogels, such as, for example, gelatin, collagen, silk, elastin, fibrin and polysaccharide-derived polymers like agarose, and chitosan, glucomannan gel, hyaluronic acid, polysaccharides, such as cross-linked carboxyl-containing polysaccharides, or a combination thereof. Synthetic hydrogels include, but are not limited to those formed from polyvinyl alcohol, acrylamides such as polyacrylic acid and poly (acrylonitrile-acrylic acid), polyurethanes, polyethylene glycol (e.g., PEG 3350, PEG 4500, PEG 8000), silicone, polyolefins such as polyisobutylene and polyisoprene, copolymers of silicone and polyurethane, neoprene, nitrile, vulcanized rubber, poly(N-vinyl-2-pyrrolidone), acrylates such as poly(2-hydroxy ethyl methacrylate) and copolymers of acrylates with N-vinyl pyrolidone, N-vinyl lactams, polyacrylonitrile or combinations thereof. The hydrogel materials may further be cross-linked to provide further strength as needed. Examples of different types of polyurethanes include thermoplastic or thermoset polyurethanes, aliphatic or aromatic polyurethanes, polyetherurethane, polycarbonate-urethane or silicone polyether-urethane, or a combination thereof.

In various embodiments, rather than directly admixing the therapeutic agents into the gel, microspheres may be dispersed within the gel, the microspheres being loaded with at least one analgesic agent and/or at least one anti-inflammatory agent. In one embodiment, the microspheres provide for a sustained release of the at least one analgesic agent and at least one anti-inflammatory agent. In yet another embodiment, the gel, which is biodegradable, prevents the microspheres from releasing the analgesic agent and/or anti-inflammatory agent; the microspheres thus do not release the analgesic agent and/or anti-inflammatory agent until they have been released from the gel. For example, a gel may be deployed around a target tissue site (e.g., a cardiac tissue). Dispersed within the gel is a plurality of microspheres that encapsulate the desired therapeutic agent. Certain of these microspheres degrade once released from the gel, thus releasing the analgesic agent and/or anti-inflammatory agent. The analgesic agents and/or anti-inflammatory agents may be placed into separate microspheres and then the microspheres combined, or the active ingredients can first be combined and then placed into the microspheres together.

Microspheres, much like a fluid, may disperse relatively quickly, depending upon the surrounding tissue type, and hence disperse the at least one analgesic agent and at least one anti-inflammatory agent. In some embodiments, the diameter of the microspheres range from about 10 microns in diameter to about 200 microns in diameter. In some embodiments they range from about 20 to 120 microns in diameters.

The present invention also contemplates the use of adherent gels to so constrain dispersal of the therapeutic agent. These gels may be deployed, for example, in the sinus cavity, or cardiac tissue, or in surrounding tissue.

Cannulas and Needles

It will be appreciated by those with skill in the art that the depot can be administered to the target site using a "cannula" or "needle" that can be a part of a drug delivery device e.g., a syringe, a gun drug delivery device, or any medical device suitable for the application of a drug to a targeted organ or anatomic region. The cannula or needle of the drug depot device is designed to cause minimal physical and psychological trauma to the patient.

Cannulas or needles include tubes that may be made from materials, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof. The cannula or needle may optionally include one or more tapered regions. In various embodiments, the cannula or needle may be beveled. The cannula or needle may also have a tip style vital for accurate treatment of the patient depending on the site for implantation. Examples of tip styles include, for example, Trephine, Cournand, Veress, Huber, Seldinger, Chiba, Francine, Bias, Crawford, deflected tips, Hustead, Lancet, or Tuohey. In various embodiments, the cannula or needle may also be non-coring and have a sheath covering it to avoid unwanted needle sticks.

The dimensions of the hollow cannula or needle, among other things, will depend on the site for implantation. The thickness of the cannula or needle will also depend on the site of implantation. In various embodiments, the thickness includes, but is not limited to, from about 0.05 to about 1.655. The gauge of the cannula or needle may be the widest or smallest diameter or a diameter in between for insertion into a human or animal body. The widest diameter is typically about 14 gauge, while the smallest diameter is about 25 gauge. In various embodiments the gauge of the needle or cannula is about 18 to about 22 gauge.

In various embodiments, like the drug depot and/or gel, the cannula or needle includes dose radiographic markers that indicate location at or near the site beneath the skin, so that the user may accurately position the depot at or near the site using any of the numerous diagnostic imaging procedures. Such diagnostic imaging procedures include, for example, X-ray imaging or fluoroscopy. Examples of such radiographic markers include, but are not limited to, barium, calcium phosphate, and/or metal beads or particles.

In various embodiments, the needle or cannula may include a transparent or translucent portion that can be visualizable by ultrasound, fluoroscopy, x-ray, or other imaging techniques. In such embodiments, the transparent or translucent portion may include a radiopaque material or ultrasound responsive topography that increases the contrast of the needle or cannula relative to the absence of the material or topography.

Sterilization

The drug depot (e.g., strip, sheet, film, etc.) and/or medical device to administer the drug depot may be sterilizable. In various embodiments, one or more components of the drug depot, and/or medical device to administer the drug depot are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity. E-beam sterilization may be used, for example, when the drug depot is included in a gel.

Other methods may also be used to sterilize the depot and/or one or more components of the device, including, but not limited to, gas sterilization, such as, for example, with ethylene oxide or steam sterilization.

Kits

In various embodiments, a kit is provided that may include additional parts along with the drug depot and/or medical device combined together to be used to implant the drug depot (e.g., film, strip, etc.). The kit may include the drug depot device in a first compartment. The second compartment may include a canister holding the drug depot and any other instruments needed for the localized drug delivery. A third compartment may include gloves, drapes, wound dressings, packing material, and other procedural supplies for maintaining sterility of the implanting process, as well as an instruction booklet. A fourth compartment may include additional cannulas and/or needles. A fifth compartment may include the agent for radiographic imaging. Each tool may be separately packaged in a plastic pouch that is radiation sterilized. A cover of the kit may include illustrations of the implanting procedure and a clear plastic cover may be placed over the compartments to maintain sterility.

Administration

In various embodiments, the analgesic and/or anti-inflammatory may be parenterally administered. The term "parenteral" as used herein refers to modes of administration, which bypass the gastrointestinal tract, and include for example, intravenous, intramuscular, continuous or intermittent infusion, intraperitoneal, intrasternal, subcutaneous, intra-operatively, intrathecally, intradiscally, peridiscally, epidurally, perispinally, intranasally, intraarticular injection or combinations thereof.

In various embodiments, a method for delivering a therapeutic agent into a surgery site of a patient is provided. The method comprising insetting a cannula at or near a target tissue site and implanting the drug depot at the target site beneath the skin of the patient and brushing, dripping, spraying, injecting, or painting the gel in the target site to hold or have the drug depot adhere to the target site. In this way unwanted migration of the drug depot away from the target site is reduced or eliminated.

In various embodiments, because the analgesic and/or anti-inflammatory agent is locally administered, therapeutically effective doses may be less than doses administered by other routes (oral, topical, etc.). For example, the drug dose delivered from the drug depot may be, for example, 10%, 20%, 30%, 40%, 50%, 60%, 70%, 80%, 90%, and 95% less than the oral dosage or injectable dose. In turn, systemic side effects, such as for example, liver transaminase elevations, hepatitis, liver failure, myopathy, constipation, etc. may be reduced or eliminated.

In various embodiments, to administer the gel having the drug depot dispersed therein to the desired site, first the cannula or needle can be inserted through the skin and soft tissue down to the target tissue site and the gel administered (e.g., brushed, dripped, injected, or painted, etc.) at or near the target site. In those embodiments where the drug depot is separate from the gel, first the cannula or needle can be inserted through the skin and soft tissue down to the site of injection and one or more base layer(s) of gel can be administered to the target site. Following administration of the one or more base layer(s), the drug depot can be implanted on or in the base layer(s) so that the gel can hold the depot in place or reduce migration. If required a subsequent layer or layers of gel can be applied on the drug depot to surround the depot and further hold it in place. Alternatively, the drug depot may be implanted first and then the gel placed (e.g., brushed, dripped, injected, or painted, etc.) around the drug depot to hold it in place. By using the gel, accurate and precise implantation of a drug depot can be accomplished with minimal physical and psychological trauma to the patient. In some embodiments, the gel may also avoid the need to suture the drug depot to the target site reducing physical and psychological trauma to the patient.

The at least one analgesic and/or anti-inflammatory agent formulation may be used to form different pharmaceutical preparations (e.g., drug depot film, sheet, strip, etc.). The pharmaceutical preparations may be formed in an administration with a suitable pharmaceutical carrier that may be solid or liquid, and placed in the appropriate form for parenteral or other administration as desired. As persons of ordinary skill are aware, known carriers include but are not limited to water, gelatin, lactose, starches, stearic acid, magnesium stearate, sicaryl alcohol, talc, vegetable oils, benzyl alcohols, gums, waxes, propylene glycol, polyalkylene glycols and other known carriers.

Another embodiment provides a method for treating a mammal suffering from pain and/or inflammation, said method comprising administering a therapeutically effective amount of the analgesic and/or anti-inflammatory agent at a target site beneath the skin at or near the target site.

In some embodiments, the therapeutically effective dosage amount (e.g., analgesic and/or anti-inflammatory) and the release rate profile are sufficient to reduce inflammation and/or pain for a period of at least one day, for example, 1-90 days, 1-10 days, 1-3 days, 3-7 days, 3-12 days; 3-14 days, 7-10 days, 7-14 days, 7-21 days, 7-30 days, 7-50 days, 7-90 days, 7-140 days, 14-140 days, 3 days to 150 days, or 3 days to 6 months.

In some embodiments the at least one analgesic and/or anti-inflammatory or a portion of the at least one analgesic and/or anti-inflammatory is administered as a bolus dose at the target tissue to provide an immediate release of the analgesic and/or anti-inflammatory.

In some embodiments there is a composition useful for the treatment of inflammation comprising an effective amount of at least one analgesic and/or anti-inflammatory that is capable of being locally administered to a target tissue site. By way of example, they may be administered locally to the nasal, sinus, and/or cardiac tissue.

In some embodiments, the at least one analgesic and/or anti-inflammatory is administered parenterally, e.g., by injection. In some embodiments, the injection is intra-cardiac, which refers to an injection into the cardiac tissue. An injection may also be into a muscle or other tissue. In other embodiments, the analgesic and/or anti-inflammatory is administered by placement into an open patient cavity during surgery.

In some embodiments, the formulation is implantable into a surgical site at the time of surgery. The active ingredients may then be released from the depot via diffusion in a sustained fashion over a period of time, e.g., 3-15 days, 5-10 days or 7-10 days post surgery in order to address pain and inflammation. In some embodiments, the active ingredient may provide longer duration of pain and/or inflammation relief for chronic diseases/conditions with release of one or more drugs up to 6 months or 1 year (e.g., 90, 100, 150, 180 days or longer).

In some embodiments, the drug depot may release 5%, 10%, 15%, 20%, 25%, 30%, 40%, 50%, 60%, 70%, 80%, 90%, 95%, or 99% of the at least one analgesic and/or anti-inflammatory agent or pharmaceutically acceptable salt thereof relative to a total amount of at least one analgesic and/or anti-inflammatory agent loaded in the drug depot over a period of 3 to 12 days, 5 to 10 days or 7 to 10 days after the drug depot is administered to the target tissue site. In some embodiments, the active ingredient may provide longer duration of pain and/or inflammation relief for chronic diseases/conditions as discussed above with release of one or more drugs up to 6 months or 1 year (e.g., 90, 100, 150, 180 days or longer).

In various embodiments, an implantable drug depot useful for reducing, preventing or treating pain and/or inflammation is provided in a patient in need of such treatment, the implantable drug depot comprising a therapeutically effective amount of a analgesic and/or anti-inflammatory agent or pharmaceutically acceptable salts thereof, the depot being implantable at a site beneath the skin to reduce, prevent or treat pain and/or inflammation, wherein the drug depot (i) comprises one or more immediate release layer(s) that is capable of releasing about 5% to about 20% of the analgesic and/or anti-inflammatory agent or pharmaceutically acceptable salts thereof relative to a total amount of the analgesic and/or anti-inflammatory agent or pharmaceutically acceptable salt thereof loaded in the drug depot over a first period of up to 48 hours and (ii) one or more sustain release layer(s) that is capable of releasing about 21% to about 99% of the analgesic and/or anti-inflammatory agent or pharmaceutically acceptable salt thereof relative to a total amount of the analgesic and/or anti-inflammatory agent or pharmaceutically acceptable salt thereof loaded in the drug depot over a subsequent period of up to 3 days to 6 months.

By way of non-limiting example, the target tissue site may comprise at least one sinus cavity, nasal cavity, cardiac tissue, muscle, ligament, tendon, cartilage, spinal disc, spinal foraminal space near the spinal nerve root, facet or spinal canal. Also by way of example, the inflammation may be associated with orthopedic or spine surgery or a combination thereof. By way of further example, the surgery may be arthroscopic surgery, an excision of a mass, hernia repair, spinal fusion, thoracic, cervical, or lumbar surgery, pelvic surgery or a combination thereof. In some embodiments, the active ingredient may provide longer duration of pain and/or inflammation relief for chronic diseases/conditions as discussed above with release of one or more drugs up to 6 months or 1 year (e.g., 90, 100, 150, 180 days or longer).

In some embodiments, the at least one analgesic and/or anti-inflammatory agent or pharmaceutically acceptable salt thereof is encapsulated in a plurality of depots comprising microparticles, microspheres, microcapsules, and/or microfibers suspended in a gel.

In some embodiments, a method is provided of inhibiting pain and/or inflammation in a patient in need of such treatment, the method comprising delivering one or more biodegradable drug depots comprising a therapeutically effective amount of at least one analgesic and/or anti-inflammatory agent or pharmaceutically acceptable salt thereof to a target tissue site beneath the skin before, during or after surgery, wherein the drug depot releases an effective amount of at least one analgesic and/or anti-inflammatory agent or pharmaceutically acceptable salt thereof over a period of 3 days to 6 months.

In some embodiments, an implantable drug depot useful for preventing or treating pain and/or inflammation in a patient in need of such treatment is provided, the implantable drug depot comprising a therapeutically effective amount of at least one analgesic and/or anti-inflammatory agent or pharmaceutically acceptable salt thereof, the depot being implantable at a site beneath the skin to prevent or treat inflammation, wherein the drug depot releases an effective amount of at least one analgesic and/or anti-inflammatory agent or pharmaceutically acceptable salt thereof over a period of 33 days to 6 months.

In some embodiments, an implantable drug depot is provided, wherein the drug depot (i) comprises one or more immediate release layer(s) that releases a bolus dose of at least one analgesic and/or anti-inflammatory agent or pharmaceutically acceptable salt thereof at a site beneath the skin and (ii) one or more sustain release layer(s) that releases an effective amount of at least one analgesic and/or anti-inflammatory agent or pharmaceutically acceptable salt thereof over a period of 3 to 12 days or 5 to 10 days or 7 to 10 days or 3 days to 6 months. By way of example, in the drug depot, the one or more immediate release layer(s) may comprise poly (lactide-co-glycolide) (PLGA) and the one or more sustain release layer(s) may comprise polylactide (PLA).

In some embodiments, an implantable drug depot useful for reducing, preventing or treating pain and inflammation in a patient is provided, the implantable drug depot in the form of a film or strip comprising a therapeutically effective amount of an analgesic and an anti-inflammatory agent or pharmaceutically acceptable salts thereof and a polymer; wherein the drug depot is implantable at a site beneath the skin to reduce, prevent or treat pain and inflammation, and the depot is capable of releasing (i) about 5% to about 20% of the analgesic or pharmaceutically acceptable salt thereof relative to a total amount of the analgesic and the anti-inflammatory agent or pharmaceutically acceptable salts thereof loaded in the drug depot over a first period of up to 72 hours and (ii) about 21% to about 99% of the analgesic and the anti-inflammatory agent or pharmaceutically acceptable salts thereof relative to a total amount of the analgesic and the anti-inflammatory agent or pharmaceutically acceptable salts thereof loaded in the drug depot over a subsequent period of up to 2 weeks.

Method of Making

In various embodiments, the drug depot comprising the active ingredients can be made by combining a biocompatible polymer and a therapeutically effective amount of the active ingredients or pharmaceutically acceptable salts thereof and forming the implantable drug depot (e.g., strip, sheet, film) from the combination.

Various techniques are available for forming at least a portion of a drug depot from the biocompatible polymer(s), therapeutic agent(s), and optional materials, including solution processing techniques and/or thermoplastic processing techniques. Where solution processing techniques are used, a solvent system is typically selected that contains one or more solvent species. The solvent system is generally a good solvent for at least one component of interest, for example, biocompatible polymer and/or therapeutic agent. The particular solvent species that make up the solvent system can also be selected based on other characteristics, including drying rate and surface tension.

Solution processing techniques include solvent casting techniques, spin coating techniques, web coating techniques, solvent spraying techniques, dipping techniques, techniques involving coating via mechanical suspension, including air suspension (e.g., fluidized coating), ink jet techniques and electrostatic techniques. Where appropriate, techniques such as those listed above can be repeated or combined to build up the depot to obtain the desired release rate and desired thickness.

In various embodiments, a solution containing solvent and biocompatible polymer are combined and placed in a mold of the desired size and shape. In this way, polymeric regions, including barrier layers, therapeutic layers, and so forth can be formed. If desired, the solution can further comprise, one or more of the following: other therapeutic agent(s) and other optional additives such as radiographic agent(s), etc. in dissolved or dispersed form. This results in a polymeric matrix region containing these species after solvent removal. In other embodiments, a solution containing solvent with dissolved or dispersed therapeutic agent is applied to a pre-existing polymeric region, which can be formed using a variety of techniques including solution processing and thermoplastic processing techniques, whereupon the therapeutic agent is imbibed into the polymeric region.

Thermoplastic processing techniques for forming the depot or portions thereof include molding techniques (for example, injection molding, rotational molding, and so forth), extrusion techniques (for example, extrusion, co-extrusion, multi-layer extrusion, and so forth) and casting.

Thermoplastic processing in accordance with various embodiments comprises mixing or compounding, in one or more stages, the biocompatible polymer(s) and one or more of the following: the active ingredients, optional additional therapeutic agent(s), radiographic agent(s), and so forth. The resulting mixture is then shaped into an implantable drug depot. The mixing and shaping operations may be performed using any of the conventional devices known in the art for such purposes.

During thermoplastic processing, there exists the potential for the therapeutic agent(s) to degrade, for example, due to elevated temperatures and/or mechanical shear that are associated with such processing. For example, certain therapeutic agents may undergo substantial degradation under ordinary thermoplastic processing conditions. Hence, processing is preferably performed under modified conditions, which prevent the substantial degradation of the therapeutic agent(s). Although it is understood that some degradation may be unavoidable during thermoplastic processing, degradation is generally limited to 10% or less. Among the processing conditions that may be controlled during processing to avoid substantial degradation of the therapeutic agent(s) are temperature, applied shear rate, applied shear stress, residence time of the mixture containing the therapeutic agent, and the technique by which the polymeric material and the therapeutic agent(s) are mixed.

Mixing or compounding biocompatible polymer with therapeutic agent(s) and any additional additives to form a substantially homogenous mixture thereof may be performed with any device known in the art and conventionally used for mixing polymeric materials with additives.

Where thermoplastic materials are employed, a polymer melt may be formed by heating the biocompatible polymer, which can be mixed with various additives (e.g., therapeutic agent(s), inactive ingredients, etc.) to form a mixture. A common way of doing so is to apply mechanical shear to a mixture of the biocompatible polymer(s) and additive(s). Devices in which the biocompatible polymer(s) and additive(s) may be mixed in this fashion include devices such as single screw extruders, twin screw extruders, banbury mixers, high-speed mixers, ross kettles, and so forth.

Any of the biocompatible polymer(s) and various additives may be premixed prior to a final thermoplastic mixing and shaping process, if desired (e.g., to prevent substantial degradation of the therapeutic agent among other reasons).

For example, in various embodiments, a biocompatible polymer is precompounded with a radiographic agent (e.g., radio-opacifying agent) under conditions of temperature and mechanical shear that would result in substantial degradation of the therapeutic agent, if it were present. This precompounded material is then mixed with therapeutic agent under conditions of lower temperature and mechanical shear, and the resulting mixture is shaped into the active ingredient containing drug depot. Conversely, in another embodiment, the biocompatible polymer can be precompounded with the therapeutic agent under conditions of reduced temperature and mechanical shear. This precompounded material is then mixed with, for example, a radio-opacifying agent, also under conditions of reduced temperature and mechanical shear, and the resulting mixture is shaped into the drug depot.

The conditions used to achieve a mixture of the biocompatible polymer and therapeutic agent and other additives will depend on a number of factors including, for example, the specific biocompatible polymer(s) and additive(s) used, as well as the type of mixing device used.

As an example, different biocompatible polymers will typically soften to facilitate mixing at different temperatures. For instance, where a depot is formed comprising PLGA or PLA polymer, a radio-opacifying agent (e.g., bismuth subcarbonate), and a therapeutic agent prone to degradation by heat and/or mechanical shear (e.g., clonidine), in various embodiments, the PGLA or PLA can be premixed with the radio-opacifying agent at temperatures of about, for example, 150° C. to 170° C. The therapeutic agent is then combined with the premixed composition and subjected to further thermoplastic processing at conditions of temperature and mechanical shear that are substantially lower than is typical for PGLA or PLA compositions. For example, where extruders are used, barrel temperature, volumetric output are typically controlled to limit the shear and therefore to prevent substantial degradation of the therapeutic agent(s). For instance, the therapeutic agent and premixed composition can be mixed/compounded using a twin screw extruder at substantially lower temperatures (e.g., 100-105° C.), and using substantially reduced volumetric output (e.g., less than 30% of full capacity, which generally corresponds to a volumetric output of less than 200 cc/min). It is noted that this processing temperature is well below the melting points of certain active ingredients, such as an anti-inflammatory and analgesic because processing at or above these temperatures will result in substantial therapeutic agent degradation. It is further noted that in certain embodiments, the processing temperature will be below the melting point of all bioactive compounds within the composition, including the therapeutic agent. After compounding, the resulting depot is shaped into the desired form, also under conditions of reduced temperature and shear.

In other embodiments, biodegradable polymer(s) and one or more therapeutic agents are premixed using non-thermoplastic techniques. For example, the biocompatible polymer can be dissolved in a solvent system containing one or more solvent species. Any desired agents (for example, a radio-opacifying agent, a therapeutic agent, or both radio-opacifying agent and therapeutic agent) can also be dissolved or dispersed in the solvents system. Solvent is then removed from the resulting solution/dispersion, forming a solid material. The resulting solid material can then be granulated for further thermoplastic processing (for example, extrusion) if desired.

As another example, the therapeutic agent can be dissolved or dispersed in a solvent system, which is then applied to a pre-existing drug depot (the pre-existing drug depot can be formed using a variety of techniques including solution and thermoplastic processing techniques, and it can comprise a variety of additives including a radio-opacifying agent and/or viscosity enhancing agent), whereupon the therapeutic agent is imbibed on or in the drug depot. As above, the resulting solid material can then be granulated for further processing, if desired.

Typically, an extrusion processes may be used to form the drug depot comprising a biocompatible polymer(s), therapeutic agent(s) and radio-opacifying agent(s). Co-extrusion may also be employed, which is a shaping process that can be used to produce a drug depot comprising the same or different layers or regions (for example, a structure comprising one or more polymeric matrix layers or regions that have permeability to fluids to allow immediate and/or sustained drug release). Multi-region depots can also be formed by other processing and shaping techniques such as co-injection or sequential injection molding technology.

In various embodiments, the depot that may emerge from the thermoplastic processing (e.g., film, strip, etc.) is cooled. Examples of cooling processes include air cooling and/or immersion in a cooling bath. In some embodiments, a water bath is used to cool the extruded depot. However, where a water-soluble therapeutic agent such as active ingredients are used, the immersion time should be held to a minimum to avoid unnecessary loss of therapeutic agent into the bath.

In various embodiments, immediate removal of water or moisture by use of ambient or warm air jets after exiting the bath will also prevent re-crystallization of the drug on the depot surface, thus controlling or minimizing a high drug dose "initial burst" or "bolus dose" upon implantation or insertion if this is release profile is not desired.

In various embodiments, the drug depot can be prepared by mixing or spraying the drug with the polymer and then molding the depot to the desired shape. In various embodiments, active ingredients are used and mixed or sprayed with the PLGA or PEG550 polymer, and the resulting depot may be formed by extrusion and dried.

In some embodiments, when the drug depot comprises a film or strip, it may be formed into a film or strip by methods such as extrusion, coating, spreading, casting or the like. If a multi-layered film or strip is desired, this may be accomplished by co-extruding more than one combination of components, which may be of the same or different composition. A multi-layered film or strip may also be achieved by coating, spreading, or casting a combination onto an already formed film layer.

Coating or casting methods are particularly useful for the purpose of forming the films or strips. Specific examples include reverse roll coating, gravure coating, immersion or dip coating, metering rod or meyer bar coating, slot die or extrusion coating, gap or knife over roll coating, air knife coating, curtain coating, or combinations thereof, especially when a multi-layered films or strips are desired.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of treating, reducing, or preventing pain or inflammation, the method comprising:
   administering three drug pellets in an epidural cavity to treat, reduce, or prevent the pain or inflammation,
   wherein each drug pellet of the three drug pellets is formed by extrusion and comprises:
      clonidine or a pharmaceutically acceptable salt, and
      a polymer comprising polylactide (PLA), D-lactide, D,L-lactide, L-lactide, or a combination thereof, the polymer comprising at least 80 wt %,
   wherein the three drug pellets are configured to release between 0.0005 μg/day and 100 μg/day of the clonidine after the administering.

2. The method of claim 1, wherein the three drug pellets are configured to release between 0.001 μg/day and 50 μg/day of the clonidine after the administering.

3. The method of claim 1, wherein the three drug pellets are configured to release between 0.001 μg/day and 35 μg/day of the clonidine after the administering.

4. The method of claim 1, wherein administering the three drug pellets comprises using a Tuohy needle.

5. The method of claim 1, wherein each drug pellet of the three drug pellets comprises an immediate release layer and a sustain release layer.

6. The method of claim 1, wherein the three drug pellets are configured to release the clonidine over a period of 7 days to 50 days after the administering.

7. The method of claim 1, wherein the three drug pellets are configured to release the clonidine over a period of 3 days to 6 months after the administering.

8. The method of claim 1, wherein the three drug pellets are configured to release between 0.001 μg/day and 35 μg/day of the clonidine after the administering, wherein each drug pellet of the three drug pellets comprises the pharmaceutically acceptable salt of clonidine, wherein each drug pellet of the three drug pellets comprises a length between 0.5 mm and 5 mm and a diameter between 0.01 mm and 2 mm, and wherein each drug pellet of the three drug pellets comprises an immediate release layer and a sustain release layer.

9. A method of treating, reducing, or preventing pain or inflammation, the method comprising:
   administering a plurality of drug pellets in an epidural cavity to treat, reduce, or prevent the pain or inflammation,
   wherein each drug pellet of the plurality of drug pellets comprises:
      clonidine or a pharmaceutically acceptable salt, and
      a polymer comprising polylactide (PLA), D-lactide, D,L-lactide, L-lactide, or a combination thereof, the polymer comprising at least 80 wt %,
   wherein the plurality of drug pellets is configured to release between 0.0005 μg/day and 100 μg/day of the clonidine after the administering.

10. The method of claim 9, wherein the plurality of drug pellets is configured to release between 0.001 μg/day and 50 μg/day of the clonidine after the administering.

11. The method of claim 9, wherein the plurality of drug pellets is configured to release between 0.001 μg/day and 35 μg/day of the clonidine after the administering.

12. The method of claim 9, wherein administering the plurality of drug pellets comprises using a Tuohy needle.

13. The method of claim 9, wherein the polymer comprises at least 80 wt %.

14. The method of claim 9, wherein each drug pellet of the plurality of drug pellets comprises an immediate release layer and a sustain release layer.

15. The method of claim 9, wherein the plurality of drug pellets is configured to release the clonidine over a period of 7 days to 50 days after the administering.

16. The method of claim 9, wherein the plurality of drug pellets is configured to release the clonidine over a period of 3 days to 6 months after the administering.

17. The method of claim 9, wherein the plurality of drug pellets is configured to release between 0.001 μg/day and 35 μg/day of the clonidine after the administering, wherein each drug pellet of the plurality of drug pellets comprises the pharmaceutically acceptable salt of clonidine, wherein each drug pellet of the plurality of drug pellets comprises a length between 0.5 mm and 5 mm and a diameter between 0.01 mm and 2 mm, wherein each drug pellet of the three drug pellets comprises an immediate release layer and a sustain release layer.

18. A method of treating, reducing, or preventing pain or inflammation, the method comprising:
   administering a drug pellet in an epidural cavity to treat, reduce, or prevent the pain or inflammation,
   wherein the drug pellet comprises:
      clonidine or a pharmaceutically acceptable salt, and
      a polymer comprising polylactide (PLA), D-lactide, D,L-lactide, L-lactide, or a combination thereof, the polymer comprising at least 80 wt %,
   wherein the drug pellet is configured to release between 0.0005 μg/day and 100 μg/day of the clonidine after the administering.

19. The method of claim 18, wherein the drug pellet is configured to release between 0.001 μg/day and 50 μg/day of the clonidine after the administering.

20. The method of claim 18, wherein the drug pellet is configured to release between 0.001 μg/day and 35 μg/day of the clonidine after the administering.

21. The method of claim 18, wherein administering the drug pellet comprises using a Tuohy needle.

22. The method of claim 18, wherein the drug pellet comprises an immediate release layer and a sustain release layer.

23. The method of claim 18, wherein the drug pellet is configured to release the clonidine over a period of 7 days to 50 days after the administering.

24. The method of claim 18, wherein the drug pellet is configured to release the clonidine over a period of 3 days to 6 months after the administering.

25. The method of claim 18, wherein the drug pellet is configured to release between 0.001 μg/day and 35 μg/day of the clonidine after the administering, wherein the drug pellet comprises the pharmaceutically acceptable salt of clonidine, and wherein the drug pellet comprises an immediate release layer and a sustain release layer.

26. The method of claim 1, wherein each drug pellet of the three drug pellets comprises a length between 0.5 mm and 5 mm and a diameter between 0.01 mm and 2 mm.

27. The method of claim 9, wherein each drug pellet of the plurality of drug pellets comprises a length between 0.5 mm and 5 mm and a diameter between 0.01 mm and 2 mm.

28. The method of claim 18, wherein the drug pellet comprises a length between 0.5 mm and 5 mm and a diameter between 0.01 mm and 2 mm.

* * * * *